US011058305B2

(12) United States Patent
Perkins et al.

(10) Patent No.: US 11,058,305 B2
(45) Date of Patent: *Jul. 13, 2021

(54) WEARABLE CUSTOMIZED EAR CANAL APPARATUS

(71) Applicant: EarLens Corporation, Menlo Park, CA (US)

(72) Inventors: Rodney Perkins, Woodside, CA (US); Brent Edwards, San Francisco, CA (US); Paul Rucker, San Francisco, CA (US); Kulbir Sandhu, Fremont, CA (US); Cem Shaquer, Saratoga, CA (US); Lakshman Rathnam, Mountain View, CA (US); William Facteau, Atherton, CA (US)

(73) Assignee: Earlens Corporation, Menlo Park, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/373,464

(22) Filed: Apr. 2, 2019

(65) Prior Publication Data
US 2019/0269336 A1    Sep. 5, 2019

Related U.S. Application Data

(63) Continuation of application No. 15/282,570, filed on Sep. 30, 2016, now Pat. No. 10,292,601.
(Continued)

(51) Int. Cl.
*A61B 5/0205* (2006.01)
*A61N 1/05* (2006.01)
(Continued)

(52) U.S. Cl.
CPC ........ *A61B 5/02055* (2013.01); *A61B 5/0059* (2013.01); *A61B 5/026* (2013.01);
(Continued)

(58) Field of Classification Search
None
See application file for complete search history.

(56) References Cited

U.S. PATENT DOCUMENTS 2,763,334 A    9/1956  Starkey
3,209,082 A    9/1965  McCarrell et al.
(Continued)

FOREIGN PATENT DOCUMENTS

AU    2004301961 A1    2/2005
CA       2242545 C     9/2009
(Continued)

OTHER PUBLICATIONS

Dictionary.com's (via American Heritage Medical Dictionary) online dictionary definition of 'percutaneous'. Accessed on Jun. 3, 2013. 2 pages.
(Continued)

*Primary Examiner* — Brian T Gedeon
(74) *Attorney, Agent, or Firm* — Wilson Sonsini Goodrich & Rosati, P.C.

(57) ABSTRACT

The present invention is directed to a wearable system wherein elements of the system, including various sensors adapted to detect biometric and other data and/or to deliver drugs, are positioned proximal to, on the ear or in the ear canal of a person. In embodiments of the invention, elements of the system are positioned on the ear or in the ear canal for extended periods of time. For example, an element of the system may be positioned on the tympanic membrane of a user and left there overnight, for multiple days, months, or years. Because of the position and longevity of the system elements in the ear canal, the present invention has many advantages over prior wearable biometric and drug delivery devices.

22 Claims, 10 Drawing Sheets

Related U.S. Application Data

(60) Provisional application No. 62/236,295, filed on Oct. 2, 2015, provisional application No. 62/395,667, filed on Sep. 16, 2016.

(51) Int. Cl.

| | |
|---|---|
| *A61B 5/00* | (2006.01) |
| *A61B 5/25* | (2021.01) |
| *H04R 25/02* | (2006.01) |
| *H04R 1/02* | (2006.01) |
| *H04R 25/00* | (2006.01) |
| *A61M 31/00* | (2006.01) |
| *A61B 5/291* | (2021.01) |
| *A61B 5/296* | (2021.01) |
| *A61B 5/349* | (2021.01) |
| *A61B 5/369* | (2021.01) |
| *A61B 5/389* | (2021.01) |
| *A61N 1/36* | (2006.01) |
| *A61B 5/026* | (2006.01) |
| *A61B 5/11* | (2006.01) |
| *A61B 5/145* | (2006.01) |
| *A61B 5/1455* | (2006.01) |
| *A61N 1/30* | (2006.01) |
| *A61M 37/00* | (2006.01) |
| *A61B 5/021* | (2006.01) |
| *A61B 5/024* | (2006.01) |
| *A61B 5/08* | (2006.01) |

(52) U.S. Cl.
CPC ............. *A61B 5/112* (2013.01); *A61B 5/1118* (2013.01); *A61B 5/14517* (2013.01); *A61B 5/14532* (2013.01); *A61B 5/14552* (2013.01); *A61B 5/25* (2021.01); *A61B 5/291* (2021.01); *A61B 5/296* (2021.01); *A61B 5/349* (2021.01); *A61B 5/369* (2021.01); *A61B 5/389* (2021.01); *A61B 5/4094* (2013.01); *A61B 5/4815* (2013.01); *A61B 5/4839* (2013.01); *A61B 5/4866* (2013.01); *A61B 5/4875* (2013.01); *A61B 5/6815* (2013.01); *A61B 5/6816* (2013.01); *A61B 5/6817* (2013.01); *A61M 31/00* (2013.01); *A61M 31/002* (2013.01); *A61N 1/0541* (2013.01); *A61N 1/306* (2013.01); *A61N 1/36036* (2017.08); *A61N 1/36038* (2017.08); *H04R 1/028* (2013.01); *H04R 25/00* (2013.01); *H04R 25/02* (2013.01); *H04R 25/70* (2013.01); *A61B 5/021* (2013.01); *A61B 5/024* (2013.01); *A61B 5/0816* (2013.01); *A61B 5/1112* (2013.01); *A61B 5/1451* (2013.01); *A61B 5/14539* (2013.01); *A61B 5/14542* (2013.01); *A61B 5/4266* (2013.01); *A61B 5/4818* (2013.01); *A61M 2037/0023* (2013.01); *A61M 2210/0662* (2013.01); *H04R 2225/023* (2013.01); *H04R 2225/025* (2013.01); *H04R 2225/55* (2013.01); *H04R 2460/07* (2013.01)

(56) References Cited

U.S. PATENT DOCUMENTS

| | | |
|---|---|---|
| 3,229,049 A | 1/1966 | Goldberg |
| 3,440,314 A | 4/1969 | Eldon |
| 3,449,768 A | 6/1969 | James |
| 3,526,949 A | 9/1970 | Frank |
| 3,549,818 A | 12/1970 | Justin |
| 3,585,416 A | 6/1971 | Howard |
| 3,594,514 A | 7/1971 | Robert |
| 3,710,399 A | 1/1973 | Hurst |
| 3,712,962 A | 1/1973 | Epley |
| 3,764,748 A | 10/1973 | Branch et al. |
| 3,808,179 A | 4/1974 | Gaylord |
| 3,870,832 A | 3/1975 | Fredrickson |
| 3,882,285 A | 5/1975 | Nunley et al. |
| 3,965,430 A | 6/1976 | Brandt |
| 3,985,977 A | 10/1976 | Beaty et al. |
| 4,002,897 A | 1/1977 | Kleinman et al. |
| 4,031,318 A | 6/1977 | Pitre |
| 4,061,972 A | 12/1977 | Burgess |
| 4,075,042 A | 2/1978 | Das |
| 4,098,277 A | 7/1978 | Mendell |
| 4,109,116 A | 8/1978 | Victoreen |
| 4,120,570 A | 10/1978 | Gaylord |
| 4,207,441 A | 6/1980 | Chouard |
| 4,248,899 A | 2/1981 | Lyon et al. |
| 4,252,440 A | 2/1981 | Frosch et al. |
| 4,281,419 A | 8/1981 | Treace |
| 4,303,772 A | 12/1981 | Novicky |
| 4,319,359 A | 3/1982 | Wolf |
| 4,334,315 A | 6/1982 | Ono et al. |
| 4,334,321 A | 6/1982 | Edelman |
| 4,338,929 A | 7/1982 | Lundin et al. |
| 4,339,954 A | 7/1982 | Anson et al. |
| 4,357,497 A | 11/1982 | Hochmair et al. |
| 4,375,016 A | 2/1983 | Harada |
| 4,380,689 A | 4/1983 | Giannetti |
| 4,428,377 A | 1/1984 | Zollner et al. |
| 4,524,294 A | 6/1985 | Brody |
| 4,540,761 A | 9/1985 | Kawamura et al. |
| 4,556,122 A | 12/1985 | Goode |
| 4,592,087 A | 5/1986 | Killion |
| 4,606,329 A | 8/1986 | Hough |
| 4,611,598 A | 9/1986 | Hortmann et al. |
| 4,628,907 A | 12/1986 | Epley |
| 4,641,377 A | 2/1987 | Rush et al. |
| 4,652,414 A | 3/1987 | Schlaegel |
| 4,654,554 A | 3/1987 | Kishi |
| 4,689,819 A | 8/1987 | Killion |
| 4,696,287 A | 9/1987 | Hortmann et al. |
| 4,729,366 A | 3/1988 | Schaefer |
| 4,741,339 A | 5/1988 | Harrison et al. |
| 4,742,499 A | 5/1988 | Butler |
| 4,756,312 A | 7/1988 | Epley |
| 4,759,070 A | 7/1988 | Voroba et al. |
| 4,766,607 A | 8/1988 | Feldman |
| 4,774,933 A | 10/1988 | Hough et al. |
| 4,776,322 A | 10/1988 | Hough et al. |
| 4,782,818 A | 11/1988 | Mori |
| 4,800,884 A | 1/1989 | Heide et al. |
| 4,800,982 A | 1/1989 | Carlson |
| 4,817,607 A | 4/1989 | Tatge |
| 4,840,178 A | 6/1989 | Heide et al. |
| 4,845,755 A | 7/1989 | Busch et al. |
| 4,865,035 A | 9/1989 | Mori |
| 4,870,688 A | 9/1989 | Voroba et al. |
| 4,918,745 A | 4/1990 | Hutchison |
| 4,932,405 A | 6/1990 | Peeters et al. |
| 4,936,305 A | 6/1990 | Ashtiani et al. |
| 4,944,301 A | 7/1990 | Widin et al. |
| 4,948,855 A | 8/1990 | Novicky |
| 4,957,478 A | 9/1990 | Maniglia et al. |
| 4,963,963 A | 10/1990 | Dorman |
| 4,982,434 A | 1/1991 | Lenhardt et al. |
| 4,999,819 A | 3/1991 | Newnham et al. |
| 5,003,608 A | 3/1991 | Carlson |
| 5,012,520 A | 4/1991 | Steeger |
| 5,015,224 A | 5/1991 | Maniglia |
| 5,015,225 A | 5/1991 | Hough et al. |
| 5,031,219 A | 7/1991 | Ward et al. |
| 5,061,282 A | 10/1991 | Jacobs |
| 5,066,091 A | 11/1991 | Stoy et al. |
| 5,068,902 A | 11/1991 | Ward |
| 5,094,108 A | 3/1992 | Kim et al. |
| 5,117,461 A | 5/1992 | Moseley |
| 5,142,186 A | 8/1992 | Cross et al. |
| 5,163,957 A | 11/1992 | Sade et al. |
| 5,167,235 A | 12/1992 | Seacord et al. |
| 5,201,007 A | 4/1993 | Ward et al. |

(56) References Cited

U.S. PATENT DOCUMENTS

| | | |
|---|---|---|
| 5,220,612 A | 6/1993 | Tibbetts et al. |
| 5,259,032 A | 11/1993 | Perkins et al. |
| 5,272,757 A | 12/1993 | Scofield et al. |
| 5,276,910 A | 1/1994 | Buchele |
| 5,277,694 A | 1/1994 | Leysieffer et al. |
| 5,282,858 A | 2/1994 | Bisch et al. |
| 5,296,797 A | 3/1994 | Bartlett |
| 5,298,692 A | 3/1994 | Ikeda et al. |
| 5,338,287 A | 8/1994 | Miller et al. |
| 5,360,388 A | 11/1994 | Spindel et al. |
| 5,378,933 A | 1/1995 | Pfannenmueller et al. |
| 5,402,496 A | 3/1995 | Soli et al. |
| 5,411,467 A | 5/1995 | Hortmann et al. |
| 5,424,698 A | 6/1995 | Dydyk et al. |
| 5,425,104 A | 6/1995 | Shennib et al. |
| 5,440,082 A | 8/1995 | Claes |
| 5,440,237 A | 8/1995 | Brown et al. |
| 5,455,994 A | 10/1995 | Termeer et al. |
| 5,456,654 A | 10/1995 | Ball |
| 5,531,787 A | 7/1996 | Lesinski et al. |
| 5,531,954 A | 7/1996 | Heide et al. |
| 5,535,282 A | 7/1996 | Luca |
| 5,554,096 A | 9/1996 | Ball |
| 5,558,618 A | 9/1996 | Maniglia |
| 5,571,148 A | 11/1996 | Loeb et al. |
| 5,572,594 A | 11/1996 | Devoe et al. |
| 5,606,621 A | 2/1997 | Reiter et al. |
| 5,624,376 A | 4/1997 | Ball et al. |
| 5,654,530 A | 8/1997 | Sauer et al. |
| 5,692,059 A | 11/1997 | Kruger |
| 5,699,809 A | 12/1997 | Combs et al. |
| 5,701,348 A | 12/1997 | Shennib et al. |
| 5,707,338 A | 1/1998 | Adams et al. |
| 5,715,321 A | 2/1998 | Andrea et al. |
| 5,721,783 A | 2/1998 | Anderson |
| 5,722,411 A | 3/1998 | Suzuki et al. |
| 5,729,077 A | 3/1998 | Newnham et al. |
| 5,740,258 A | 4/1998 | Goodwin-Johansson |
| 5,742,692 A | 4/1998 | Garcia et al. |
| 5,749,912 A | 5/1998 | Zhang et al. |
| 5,762,583 A | 6/1998 | Adams et al. |
| 5,772,575 A | 6/1998 | Lesinski et al. |
| 5,774,259 A | 6/1998 | Saitoh et al. |
| 5,782,744 A | 7/1998 | Money |
| 5,788,711 A | 8/1998 | Lehner et al. |
| 5,795,287 A | 8/1998 | Ball et al. |
| 5,797,834 A | 8/1998 | Goode |
| 5,800,336 A | 9/1998 | Ball et al. |
| 5,804,109 A | 9/1998 | Perkins |
| 5,804,907 A | 9/1998 | Park et al. |
| 5,814,095 A | 9/1998 | Mueller et al. |
| 5,824,022 A | 10/1998 | Zilberman et al. |
| 5,825,122 A | 10/1998 | Givargizov et al. |
| 5,836,863 A | 11/1998 | Bushek et al. |
| 5,842,967 A | 12/1998 | Kroll |
| 5,851,199 A | 12/1998 | Peerless et al. |
| 5,857,958 A | 1/1999 | Ball et al. |
| 5,859,916 A | 1/1999 | Ball et al. |
| 5,868,682 A | 2/1999 | Combs et al. |
| 5,879,283 A | 3/1999 | Adams et al. |
| 5,888,187 A | 3/1999 | Jaeger et al. |
| 5,897,486 A | 4/1999 | Ball et al. |
| 5,899,847 A | 5/1999 | Adams et al. |
| 5,900,274 A | 5/1999 | Chatterjee et al. |
| 5,906,635 A | 5/1999 | Maniglia |
| 5,913,815 A | 6/1999 | Ball et al. |
| 5,922,017 A | 7/1999 | Bredberg et al. |
| 5,922,077 A | 7/1999 | Espy et al. |
| 5,935,170 A | 8/1999 | Haakansson et al. |
| 5,940,519 A | 8/1999 | Kuo |
| 5,949,895 A | 9/1999 | Ball et al. |
| 5,951,601 A | 9/1999 | Lesinski et al. |
| 5,984,859 A | 11/1999 | Lesinski |
| 5,987,146 A | 11/1999 | Pluvinage et al. |
| 6,001,129 A | 12/1999 | Bushek et al. |
| 6,005,955 A | 12/1999 | Kroll et al. |
| 6,011,984 A | 1/2000 | Van et al. |
| 6,024,717 A | 2/2000 | Ball et al. |
| 6,038,480 A | 3/2000 | Hrdlicka et al. |
| 6,045,528 A | 4/2000 | Arenberg et al. |
| 6,050,933 A | 4/2000 | Bushek et al. |
| 6,067,474 A | 5/2000 | Schulman et al. |
| 6,068,589 A | 5/2000 | Neukermans |
| 6,068,590 A | 5/2000 | Brisken |
| 6,072,884 A | 6/2000 | Kates |
| 6,084,975 A | 7/2000 | Perkins |
| 6,093,144 A | 7/2000 | Jaeger et al. |
| 6,135,612 A | 10/2000 | Clore |
| 6,137,889 A | 10/2000 | Shennib et al. |
| 6,139,488 A | 10/2000 | Ball |
| 6,153,966 A | 11/2000 | Neukermans |
| 6,168,948 B1 | 1/2001 | Anderson et al. |
| 6,174,278 B1 | 1/2001 | Jaeger et al. |
| 6,175,637 B1 | 1/2001 | Fujihira et al. |
| 6,181,801 B1 | 1/2001 | Puthuff et al. |
| 6,190,305 B1 | 2/2001 | Ball et al. |
| 6,190,306 B1 | 2/2001 | Kennedy |
| 6,208,445 B1 | 3/2001 | Reime |
| 6,216,040 B1 | 4/2001 | Harrison |
| 6,217,508 B1 | 4/2001 | Ball et al. |
| 6,219,427 B1 | 4/2001 | Kates et al. |
| 6,222,302 B1 | 4/2001 | Imada et al. |
| 6,222,927 B1 | 4/2001 | Feng et al. |
| 6,240,192 B1 | 5/2001 | Brennan et al. |
| 6,241,767 B1 | 6/2001 | Stennert et al. |
| 6,259,951 B1 | 7/2001 | Kuzma et al. |
| 6,261,224 B1 | 7/2001 | Adams et al. |
| 6,264,603 B1 | 7/2001 | Kennedy |
| 6,277,148 B1 | 8/2001 | Dormer |
| 6,312,959 B1 | 11/2001 | Datskos |
| 6,339,648 B1 | 1/2002 | McIntosh et al. |
| 6,342,035 B1 | 1/2002 | Kroll et al. |
| 6,354,990 B1 | 3/2002 | Juneau et al. |
| 6,359,993 B2 | 3/2002 | Brimhall |
| 6,366,863 B1 | 4/2002 | Bye et al. |
| 6,374,143 B1 | 4/2002 | Berrang et al. |
| 6,385,363 B1 | 5/2002 | Rajic et al. |
| 6,387,039 B1 | 5/2002 | Moses |
| 6,390,971 B1 | 5/2002 | Adams et al. |
| 6,393,130 B1 | 5/2002 | Stonikas et al. |
| 6,422,991 B1 | 7/2002 | Jaeger |
| 6,432,248 B1 | 8/2002 | Popp et al. |
| 6,434,246 B1 | 8/2002 | Kates et al. |
| 6,434,247 B1 | 8/2002 | Kates et al. |
| 6,436,028 B1 | 8/2002 | Dormer |
| 6,438,244 B1 | 8/2002 | Juneau et al. |
| 6,445,799 B1 | 9/2002 | Taenzer et al. |
| 6,473,512 B1 | 10/2002 | Juneau et al. |
| 6,475,134 B1 | 11/2002 | Ball et al. |
| 6,491,622 B1 | 12/2002 | Kasic, II et al. |
| 6,491,644 B1 | 12/2002 | Vujanic et al. |
| 6,491,722 B1 | 12/2002 | Kroll et al. |
| 6,493,453 B1 | 12/2002 | Glendon |
| 6,493,454 B1 | 12/2002 | Loi et al. |
| 6,498,858 B2 | 12/2002 | Kates |
| 6,507,758 B1 | 1/2003 | Greenberg et al. |
| 6,519,376 B2 | 2/2003 | Biagi et al. |
| 6,523,985 B2 | 2/2003 | Hamanaka et al. |
| 6,536,530 B2 | 3/2003 | Schultz et al. |
| 6,537,200 B2 | 3/2003 | Leysieffer et al. |
| 6,547,715 B1 | 4/2003 | Mueller et al. |
| 6,549,633 B1 | 4/2003 | Westermann |
| 6,549,635 B1 | 4/2003 | Gebert |
| 6,554,761 B1 | 4/2003 | Puria et al. |
| 6,575,894 B2 | 6/2003 | Leysieffer et al. |
| 6,592,513 B1 | 7/2003 | Kroll et al. |
| 6,603,860 B1 | 8/2003 | Taenzer et al. |
| 6,620,110 B2 | 9/2003 | Schmid |
| 6,626,822 B1 | 9/2003 | Jaeger et al. |
| 6,629,922 B1 | 10/2003 | Puria et al. |
| 6,631,196 B1 | 10/2003 | Taenzer et al. |
| 6,643,378 B2 | 11/2003 | Schumaier |
| 6,663,575 B2 | 12/2003 | Leysieffer |
| 6,668,062 B1 | 12/2003 | Luo et al. |

(56) References Cited

U.S. PATENT DOCUMENTS

| | | |
|---|---|---|
| 6,676,592 B2 | 1/2004 | Ball et al. |
| 6,681,022 B1 | 1/2004 | Puthuff et al. |
| 6,695,943 B2 | 2/2004 | Juneau et al. |
| 6,697,674 B2 | 2/2004 | Leysieffer |
| 6,724,902 B1 | 4/2004 | Shennib et al. |
| 6,726,618 B2 | 4/2004 | Miller |
| 6,726,718 B1 | 4/2004 | Carlyle et al. |
| 6,727,789 B2 | 4/2004 | Tibbetts et al. |
| 6,728,024 B2 | 4/2004 | Ribak |
| 6,735,318 B2 | 5/2004 | Cho |
| 6,754,358 B1 | 6/2004 | Boesen et al. |
| 6,754,359 B1 | 6/2004 | Svean et al. |
| 6,754,537 B1 | 6/2004 | Harrison et al. |
| 6,785,394 B1 | 8/2004 | Olsen et al. |
| 6,792,114 B1 | 9/2004 | Kates et al. |
| 6,801,629 B2 | 10/2004 | Brimhall et al. |
| 6,829,363 B2 | 12/2004 | Sacha |
| 6,831,986 B2 | 12/2004 | Kates |
| 6,837,857 B2 | 1/2005 | Stirnemann |
| 6,842,647 B1 | 1/2005 | Griffith et al. |
| 6,888,949 B1 | 5/2005 | Vanden et al. |
| 6,900,926 B2 | 5/2005 | Ribak |
| 6,912,289 B2 | 6/2005 | Vonlanthen et al. |
| 6,920,340 B2 | 7/2005 | Laderman |
| 6,931,231 B1 | 8/2005 | Griffin |
| 6,940,988 B1 | 9/2005 | Shennib et al. |
| 6,940,989 B1 | 9/2005 | Shennib et al. |
| D512,979 S | 12/2005 | Corcoran et al. |
| 6,975,402 B2 | 12/2005 | Bisson et al. |
| 6,978,159 B2 | 12/2005 | Feng et al. |
| 7,020,297 B2 | 3/2006 | Fang et al. |
| 7,024,010 B2 | 4/2006 | Saunders et al. |
| 7,043,037 B2 | 5/2006 | Lichtblau et al. |
| 7,050,675 B2 | 5/2006 | Zhou et al. |
| 7,050,876 B1 | 5/2006 | Fu et al. |
| 7,057,256 B2 | 6/2006 | Mazur et al. |
| 7,058,182 B2 | 6/2006 | Kates |
| 7,058,188 B1 | 6/2006 | Allred |
| 7,072,475 B1 | 7/2006 | Denap et al. |
| 7,076,076 B2 | 7/2006 | Bauman |
| 7,095,981 B1 | 8/2006 | Voroba et al. |
| 7,167,572 B1 | 1/2007 | Harrison et al. |
| 7,174,026 B2 | 2/2007 | Niederdrank et al. |
| 7,179,238 B2 | 2/2007 | Hissong |
| 7,181,034 B2 | 2/2007 | Armstrong |
| 7,203,331 B2 | 4/2007 | Boesen |
| 7,239,069 B2 | 7/2007 | Cho |
| 7,245,732 B2 | 7/2007 | Jorgensen et al. |
| 7,255,457 B2 | 8/2007 | Ducharme et al. |
| 7,266,208 B2 | 9/2007 | Charvin et al. |
| 7,289,639 B2 | 10/2007 | Abel et al. |
| 7,313,245 B1 | 12/2007 | Shennib |
| 7,315,211 B1 | 1/2008 | Lee et al. |
| 7,322,930 B2 | 1/2008 | Jaeger et al. |
| 7,349,741 B2 | 3/2008 | Maltan et al. |
| 7,354,792 B2 | 4/2008 | Mazur et al. |
| 7,376,563 B2 | 5/2008 | Leysieffer et al. |
| 7,390,689 B2 | 6/2008 | Mazur et al. |
| 7,394,909 B1 | 7/2008 | Widmer et al. |
| 7,421,087 B2 | 9/2008 | Perkins et al. |
| 7,424,122 B2 | 9/2008 | Ryan |
| 7,444,877 B2 | 11/2008 | Li et al. |
| 7,547,275 B2 | 6/2009 | Cho et al. |
| 7,630,646 B2 | 12/2009 | Anderson et al. |
| 7,645,877 B2 | 1/2010 | Gmeiner et al. |
| 7,668,325 B2 | 2/2010 | Puria et al. |
| 7,747,295 B2 | 6/2010 | Choi |
| 7,778,434 B2 | 8/2010 | Juneau et al. |
| 7,809,150 B2 | 10/2010 | Natarajan et al. |
| 7,822,215 B2 | 10/2010 | Carazo et al. |
| 7,826,632 B2 | 11/2010 | Von et al. |
| 7,853,033 B2 | 12/2010 | Maltan et al. |
| 7,867,160 B2 | 1/2011 | Pluvinage et al. |
| 7,883,535 B2 | 2/2011 | Cantin et al. |
| 7,885,359 B2 | 2/2011 | Meltzer |
| 7,983,435 B2 | 7/2011 | Moses |
| 8,090,134 B2 | 1/2012 | Takigawa et al. |
| 8,116,494 B2 | 2/2012 | Rass |
| 8,128,551 B2 | 3/2012 | Jolly |
| 8,157,730 B2 | 4/2012 | Leboeuf et al. |
| 8,197,461 B1 | 6/2012 | Arenberg et al. |
| 8,204,786 B2 | 6/2012 | Leboeuf et al. |
| 8,233,651 B1 | 7/2012 | Haller |
| 8,251,903 B2 | 8/2012 | Leboeuf et al. |
| 8,284,970 B2 | 10/2012 | Sacha |
| 8,295,505 B2 | 10/2012 | Weinans et al. |
| 8,295,523 B2 | 10/2012 | Fay et al. |
| 8,320,601 B2 | 11/2012 | Takigawa et al. |
| 8,320,982 B2 | 11/2012 | Leboeuf et al. |
| 8,340,310 B2 | 12/2012 | Ambrose et al. |
| 8,340,335 B1 | 12/2012 | Shennib |
| 8,391,527 B2 | 3/2013 | Feucht et al. |
| 8,396,235 B2 | 3/2013 | Gebhardt et al. |
| 8,396,239 B2 | 3/2013 | Fay et al. |
| 8,401,212 B2 | 3/2013 | Puria et al. |
| 8,401,214 B2 | 3/2013 | Perkins et al. |
| 8,506,473 B2 | 8/2013 | Puria |
| 8,512,242 B2 | 8/2013 | Leboeuf et al. |
| 8,526,651 B2 | 9/2013 | Van et al. |
| 8,526,652 B2 | 9/2013 | Ambrose et al. |
| 8,526,971 B2 | 9/2013 | Giniger et al. |
| 8,545,383 B2 | 10/2013 | Wenzel et al. |
| 8,600,089 B2 | 12/2013 | Wenzel et al. |
| 8,647,270 B2 | 2/2014 | Leboeuf et al. |
| 8,652,040 B2 | 2/2014 | Leboeuf et al. |
| 8,684,922 B2 | 4/2014 | Tran |
| 8,696,054 B2 | 4/2014 | Crum |
| 8,696,541 B2 | 4/2014 | Pluvinage et al. |
| 8,700,111 B2 | 4/2014 | Leboeuf et al. |
| 8,702,607 B2 | 4/2014 | Leboeuf et al. |
| 8,715,152 B2 | 5/2014 | Puria et al. |
| 8,715,153 B2 | 5/2014 | Puria et al. |
| 8,715,154 B2 | 5/2014 | Perkins et al. |
| 8,761,423 B2 | 6/2014 | Wagner et al. |
| 8,787,609 B2 | 7/2014 | Perkins et al. |
| 8,788,002 B2 | 7/2014 | Leboeuf et al. |
| 8,817,998 B2 | 8/2014 | Inoue |
| 8,824,715 B2 | 9/2014 | Fay et al. |
| 8,837,758 B2 | 9/2014 | Knudsen |
| 8,845,705 B2 | 9/2014 | Perkins et al. |
| 8,855,323 B2 | 10/2014 | Kroman |
| 8,858,419 B2 | 10/2014 | Puria et al. |
| 8,885,860 B2 | 11/2014 | Djalilian et al. |
| 8,886,269 B2 | 11/2014 | Leboeuf et al. |
| 8,888,701 B2 | 11/2014 | Leboeuf et al. |
| 8,923,941 B2 | 12/2014 | Leboeuf et al. |
| 8,929,965 B2 | 1/2015 | Leboeuf et al. |
| 8,929,966 B2 | 1/2015 | Leboeuf et al. |
| 8,934,952 B2 | 1/2015 | Leboeuf et al. |
| 8,942,776 B2 | 1/2015 | Leboeuf et al. |
| 8,961,415 B2 | 2/2015 | Leboeuf et al. |
| 8,986,187 B2 | 3/2015 | Perkins et al. |
| 8,989,830 B2 | 3/2015 | Leboeuf et al. |
| 9,044,180 B2 | 6/2015 | Leboeuf et al. |
| 9,049,528 B2 | 6/2015 | Jonathan et al. |
| 9,055,379 B2 | 6/2015 | Puria et al. |
| 9,131,312 B2 | 9/2015 | Leboeuf et al. |
| 9,154,891 B2 | 10/2015 | Puria et al. |
| 9,211,069 B2 | 12/2015 | Larsen et al. |
| 9,226,083 B2 | 12/2015 | Puria et al. |
| 9,277,335 B2 | 3/2016 | Perkins et al. |
| 9,289,135 B2 | 3/2016 | Leboeuf et al. |
| 9,289,175 B2 | 3/2016 | Leboeuf et al. |
| 9,301,696 B2 | 4/2016 | Leboeuf et al. |
| 9,314,167 B2 | 4/2016 | Leboeuf et al. |
| 9,392,377 B2 | 7/2016 | Olsen et al. |
| 9,427,191 B2 | 8/2016 | Leboeuf et al. |
| 9,497,556 B2 | 11/2016 | Kaltenbacher et al. |
| 9,521,962 B2 | 12/2016 | Leboeuf |
| 9,524,092 B2 | 12/2016 | Ren et al. |
| 9,538,921 B2 | 1/2017 | Leboeuf et al. |
| 9,544,700 B2 | 1/2017 | Puria et al. |
| 9,564,862 B2 | 2/2017 | Hoyerby |
| 9,591,409 B2 | 3/2017 | Puria et al. |

(56) References Cited

U.S. PATENT DOCUMENTS

| | | |
|---|---|---|
| 9,749,758 B2 | 8/2017 | Puria et al. |
| 9,750,462 B2 | 9/2017 | Leboeuf et al. |
| 9,788,785 B2 | 10/2017 | Leboeuf |
| 9,788,794 B2 | 10/2017 | Leboeuf et al. |
| 9,794,653 B2 | 10/2017 | Aumer et al. |
| 9,801,552 B2 | 10/2017 | Romesburg et al. |
| 9,808,204 B2 | 11/2017 | Leboeuf et al. |
| 9,924,276 B2 | 3/2018 | Wenzel |
| 9,930,458 B2 | 3/2018 | Freed et al. |
| 9,949,035 B2 | 4/2018 | Rucker et al. |
| 9,949,039 B2 | 4/2018 | Puria et al. |
| 9,949,045 B2 | 4/2018 | Kure et al. |
| 9,961,454 B2 | 5/2018 | Puria et al. |
| 9,964,672 B2 | 5/2018 | Phair et al. |
| 10,003,888 B2 | 6/2018 | Stephanou et al. |
| 10,034,103 B2 | 7/2018 | Puria et al. |
| 10,154,352 B2 | 12/2018 | Perkins et al. |
| 10,178,483 B2 | 1/2019 | Teran et al. |
| 10,206,045 B2 | 2/2019 | Kaltenbacher et al. |
| 10,237,663 B2 | 3/2019 | Puria et al. |
| 10,284,964 B2 | 5/2019 | Olsen et al. |
| 10,286,215 B2 | 5/2019 | Perkins et al. |
| 10,292,601 B2 | 5/2019 | Perkins et al. |
| 10,492,010 B2 | 11/2019 | Rucker et al. |
| 10,511,913 B2 | 12/2019 | Puria et al. |
| 10,516,946 B2 | 12/2019 | Puria et al. |
| 10,516,949 B2 | 12/2019 | Puria et al. |
| 10,516,950 B2 | 12/2019 | Perkins et al. |
| 10,516,951 B2 | 12/2019 | Wenzel |
| 10,531,206 B2 | 1/2020 | Freed et al. |
| 10,609,492 B2 | 3/2020 | Olsen et al. |
| 10,743,110 B2 | 8/2020 | Puria et al. |
| 10,779,094 B2 | 9/2020 | Rucker et al. |
| 10,863,286 B2 | 12/2020 | Perkins et al. |
| 2001/0003788 A1 | 6/2001 | Ball et al. |
| 2001/0007050 A1 | 7/2001 | Adelman |
| 2001/0024507 A1 | 9/2001 | Boesen |
| 2001/0027342 A1 | 10/2001 | Dormer |
| 2001/0029313 A1 | 10/2001 | Kennedy |
| 2001/0043708 A1 | 11/2001 | Brimhall |
| 2001/0053871 A1 | 12/2001 | Zilberman et al. |
| 2001/0055405 A1 | 12/2001 | Cho |
| 2002/0012438 A1 | 1/2002 | Leysieffer et al. |
| 2002/0025055 A1 | 2/2002 | Stonikas et al. |
| 2002/0029070 A1 | 3/2002 | Leysieffer et al. |
| 2002/0030871 A1 | 3/2002 | Anderson et al. |
| 2002/0035309 A1 | 3/2002 | Leysieffer |
| 2002/0048374 A1 | 4/2002 | Soli et al. |
| 2002/0085728 A1 | 7/2002 | Shennib et al. |
| 2002/0086715 A1 | 7/2002 | Sahagen |
| 2002/0172350 A1 | 11/2002 | Edwards et al. |
| 2002/0183587 A1 | 12/2002 | Dormer |
| 2003/0021903 A1 | 1/2003 | Shlenker et al. |
| 2003/0055311 A1 | 3/2003 | Neukermans et al. |
| 2003/0064746 A1 | 4/2003 | Rader et al. |
| 2003/0081803 A1 | 5/2003 | Petilli et al. |
| 2003/0097178 A1 | 5/2003 | Roberson et al. |
| 2003/0125602 A1 | 7/2003 | Sokolich et al. |
| 2003/0142841 A1 | 7/2003 | Wiegand |
| 2003/0208099 A1 | 11/2003 | Ball |
| 2003/0208888 A1 | 11/2003 | Fearing et al. |
| 2003/0220536 A1 | 11/2003 | Hissong |
| 2004/0019294 A1 | 1/2004 | Stirnemann |
| 2004/0093040 A1 | 5/2004 | Boylston et al. |
| 2004/0121291 A1 | 6/2004 | Knapp et al. |
| 2004/0158157 A1 | 8/2004 | Jensen et al. |
| 2004/0165742 A1 | 8/2004 | Shennib et al. |
| 2004/0166495 A1 | 8/2004 | Greinwald et al. |
| 2004/0167377 A1 | 8/2004 | Schafer et al. |
| 2004/0184732 A1 | 9/2004 | Zhou et al. |
| 2004/0190734 A1 | 9/2004 | Kates |
| 2004/0202339 A1 | 10/2004 | O'Brien et al. |
| 2004/0202340 A1 | 10/2004 | Armstrong et al. |
| 2004/0208333 A1 | 10/2004 | Cheung et al. |
| 2004/0234089 A1 | 11/2004 | Rembrand et al. |
| 2004/0234092 A1 | 11/2004 | Wada et al. |
| 2004/0236416 A1 | 11/2004 | Falotico |
| 2004/0240691 A1 | 12/2004 | Grafenberg |
| 2005/0018859 A1 | 1/2005 | Buchholz |
| 2005/0020873 A1 | 1/2005 | Berrang et al. |
| 2005/0036639 A1 | 2/2005 | Bachler et al. |
| 2005/0038498 A1 | 2/2005 | Dubrow et al. |
| 2005/0088435 A1 | 4/2005 | Geng |
| 2005/0101830 A1 | 5/2005 | Easter et al. |
| 2005/0111683 A1 | 5/2005 | Chabries et al. |
| 2005/0117765 A1 | 6/2005 | Meyer et al. |
| 2005/0163333 A1 | 7/2005 | Abel et al. |
| 2005/0190939 A1 | 9/2005 | Fretz et al. |
| 2005/0196005 A1 | 9/2005 | Shennib et al. |
| 2005/0222823 A1 | 10/2005 | Brumback et al. |
| 2005/0226446 A1 | 10/2005 | Luo et al. |
| 2005/0267549 A1 | 12/2005 | Della et al. |
| 2005/0271870 A1 | 12/2005 | Jackson |
| 2005/0288739 A1 | 12/2005 | Hassler, Jr. et al. |
| 2006/0015155 A1 | 1/2006 | Charvin et al. |
| 2006/0023908 A1 | 2/2006 | Perkins et al. |
| 2006/0058573 A1 | 3/2006 | Neisz et al. |
| 2006/0062420 A1 | 3/2006 | Araki |
| 2006/0074159 A1 | 4/2006 | Lu et al. |
| 2006/0075175 A1 | 4/2006 | Jensen et al. |
| 2006/0107744 A1 | 5/2006 | Li et al. |
| 2006/0129210 A1 | 6/2006 | Cantin et al. |
| 2006/0161227 A1 | 7/2006 | Walsh et al. |
| 2006/0161255 A1 | 7/2006 | Zarowski et al. |
| 2006/0177079 A1 | 8/2006 | Baekgaard et al. |
| 2006/0177082 A1 | 8/2006 | Solomito et al. |
| 2006/0183965 A1 | 8/2006 | Kasic et al. |
| 2006/0189841 A1 | 8/2006 | Pluvinage et al. |
| 2006/0231914 A1 | 10/2006 | Carey, III |
| 2006/0233398 A1 | 10/2006 | Husung |
| 2006/0237126 A1 | 10/2006 | Guffrey et al. |
| 2006/0247735 A1 | 11/2006 | Honert et al. |
| 2006/0251278 A1 | 11/2006 | Puria et al. |
| 2006/0256989 A1 | 11/2006 | Olsen et al. |
| 2006/0278245 A1 | 12/2006 | Gan |
| 2007/0030990 A1 | 2/2007 | Fischer |
| 2007/0036377 A1 | 2/2007 | Stirnemann |
| 2007/0076913 A1 | 4/2007 | Schanz |
| 2007/0083078 A1 | 4/2007 | Easter et al. |
| 2007/0100197 A1 | 5/2007 | Perkins et al. |
| 2007/0127748 A1 | 6/2007 | Carlile et al. |
| 2007/0127752 A1 | 6/2007 | Armstrong |
| 2007/0127766 A1 | 6/2007 | Combest |
| 2007/0135870 A1 | 6/2007 | Shanks et al. |
| 2007/0161848 A1 | 7/2007 | Dalton et al. |
| 2007/0191673 A1 | 8/2007 | Ball et al. |
| 2007/0201713 A1 | 8/2007 | Fang et al. |
| 2007/0206825 A1 | 9/2007 | Thomasson |
| 2007/0223755 A1 | 9/2007 | Salvetti et al. |
| 2007/0225776 A1 | 9/2007 | Fritsch et al. |
| 2007/0236704 A1 | 10/2007 | Carr et al. |
| 2007/0250119 A1 | 10/2007 | Tyler et al. |
| 2007/0251082 A1 | 11/2007 | Milojevic et al. |
| 2007/0258507 A1 | 11/2007 | Lee et al. |
| 2007/0286429 A1 | 12/2007 | Grafenberg et al. |
| 2008/0021518 A1 | 1/2008 | Hochmair et al. |
| 2008/0051623 A1 | 2/2008 | Schneider et al. |
| 2008/0054509 A1 | 3/2008 | Berman et al. |
| 2008/0063228 A1 | 3/2008 | Mejia et al. |
| 2008/0063231 A1 | 3/2008 | Juneau et al. |
| 2008/0064918 A1 | 3/2008 | Jolly |
| 2008/0077198 A1 | 3/2008 | Webb et al. |
| 2008/0089292 A1 | 4/2008 | Kitazoe et al. |
| 2008/0107292 A1 | 5/2008 | Kornagel |
| 2008/0123866 A1 | 5/2008 | Rule et al. |
| 2008/0130927 A1 | 6/2008 | Theverapperuma et al. |
| 2008/0188707 A1 | 8/2008 | Bernard et al. |
| 2008/0298600 A1 | 12/2008 | Poe et al. |
| 2008/0300703 A1 | 12/2008 | Widmer et al. |
| 2009/0016553 A1 | 1/2009 | Ho et al. |
| 2009/0023976 A1 | 1/2009 | Cho et al. |
| 2009/0043149 A1 | 2/2009 | Abel et al. |
| 2009/0076581 A1 | 3/2009 | Gibson |
| 2009/0092271 A1 | 4/2009 | Fay et al. |

(56) References Cited

U.S. PATENT DOCUMENTS

| | | |
|---|---|---|
| 2009/0097681 A1 | 4/2009 | Puria et al. |
| 2009/0131742 A1 | 5/2009 | Cho et al. |
| 2009/0141919 A1 | 6/2009 | Spitaels et al. |
| 2009/0149697 A1 | 6/2009 | Steinhardt et al. |
| 2009/0157143 A1 | 6/2009 | Edler et al. |
| 2009/0175474 A1 | 7/2009 | Salvetti et al. |
| 2009/0246627 A1 | 10/2009 | Park |
| 2009/0253951 A1 | 10/2009 | Ball et al. |
| 2009/0262966 A1 | 10/2009 | Vestergaard et al. |
| 2009/0281367 A1 | 11/2009 | Cho et al. |
| 2009/0310805 A1 | 12/2009 | Petroff |
| 2009/0316922 A1 | 12/2009 | Merks et al. |
| 2010/0034409 A1 | 2/2010 | Fay et al. |
| 2010/0036488 A1 | 2/2010 | De, Jr. et al. |
| 2010/0048982 A1 | 2/2010 | Puria et al. |
| 2010/0085176 A1 | 4/2010 | Flick |
| 2010/0103404 A1 | 4/2010 | Remke et al. |
| 2010/0111315 A1 | 5/2010 | Kroman |
| 2010/0114190 A1 | 5/2010 | Bendett et al. |
| 2010/0145135 A1 | 6/2010 | Ball et al. |
| 2010/0152527 A1 | 6/2010 | Puria |
| 2010/0171369 A1 | 7/2010 | Baarman et al. |
| 2010/0172507 A1 | 7/2010 | Merks |
| 2010/0177918 A1 | 7/2010 | Keady et al. |
| 2010/0202645 A1 | 8/2010 | Puria et al. |
| 2010/0222639 A1 | 9/2010 | Purcell et al. |
| 2010/0260364 A1 | 10/2010 | Merks |
| 2010/0272299 A1 | 10/2010 | Van et al. |
| 2010/0290653 A1 | 11/2010 | Wiggins et al. |
| 2010/0312040 A1 | 12/2010 | Puria et al. |
| 2011/0062793 A1 | 3/2011 | Azancot et al. |
| 2011/0069852 A1 | 3/2011 | Arndt et al. |
| 2011/0077453 A1 | 3/2011 | Pluvinage et al. |
| 2011/0084654 A1 | 4/2011 | Julstrom et al. |
| 2011/0112462 A1 | 5/2011 | Parker et al. |
| 2011/0116666 A1 | 5/2011 | Dittberner et al. |
| 2011/0125222 A1 | 5/2011 | Perkins et al. |
| 2011/0130622 A1 | 6/2011 | Ilberg et al. |
| 2011/0142274 A1 | 6/2011 | Perkins et al. |
| 2011/0144414 A1 | 6/2011 | Spearman et al. |
| 2011/0152601 A1 | 6/2011 | Puria et al. |
| 2011/0152602 A1 | 6/2011 | Perkins et al. |
| 2011/0152603 A1 | 6/2011 | Perkins et al. |
| 2011/0152976 A1 | 6/2011 | Perkins et al. |
| 2011/0164771 A1 | 7/2011 | Jensen et al. |
| 2011/0182453 A1 | 7/2011 | Van et al. |
| 2011/0196460 A1 | 8/2011 | Weiss |
| 2011/0221391 A1 | 9/2011 | Won et al. |
| 2011/0249845 A1 | 10/2011 | Kates |
| 2011/0249847 A1 | 10/2011 | Salvetti et al. |
| 2011/0257290 A1 | 10/2011 | Zeller et al. |
| 2011/0258839 A1 | 10/2011 | Probst |
| 2011/0271965 A1 | 11/2011 | Parkins et al. |
| 2012/0008807 A1 | 1/2012 | Gran |
| 2012/0014546 A1 | 1/2012 | Puria et al. |
| 2012/0038881 A1 | 2/2012 | Amirparviz et al. |
| 2012/0039493 A1 | 2/2012 | Rucker et al. |
| 2012/0092461 A1 | 4/2012 | Fisker et al. |
| 2012/0114157 A1 | 5/2012 | Arndt et al. |
| 2012/0140967 A1 | 6/2012 | Aubert et al. |
| 2012/0217087 A1 | 8/2012 | Ambrose et al. |
| 2012/0236524 A1 | 9/2012 | Pugh et al. |
| 2012/0263339 A1 | 10/2012 | Funahashi |
| 2013/0004004 A1 | 1/2013 | Zhao et al. |
| 2013/0034258 A1 | 2/2013 | Lin |
| 2013/0083938 A1 | 4/2013 | Bakalos et al. |
| 2013/0089227 A1 | 4/2013 | Kates |
| 2013/0195300 A1 | 8/2013 | Larsen et al. |
| 2013/0230204 A1 | 9/2013 | Monahan et al. |
| 2013/0287239 A1 | 10/2013 | Fay et al. |
| 2013/0303835 A1 | 11/2013 | Koskowich |
| 2013/0308782 A1 | 11/2013 | Dittberner et al. |
| 2013/0308807 A1 | 11/2013 | Burns |
| 2013/0315428 A1 | 11/2013 | Perkins et al. |
| 2013/0343584 A1 | 12/2013 | Bennett et al. |
| 2013/0343585 A1 | 12/2013 | Bennett et al. |
| 2013/0343587 A1 | 12/2013 | Naylor et al. |
| 2014/0003640 A1 | 1/2014 | Puria et al. |
| 2014/0056453 A1 | 2/2014 | Olsen et al. |
| 2014/0084698 A1 | 3/2014 | Asanuma et al. |
| 2014/0107423 A1 | 4/2014 | Yaacobi |
| 2014/0153761 A1 | 6/2014 | Shennib et al. |
| 2014/0169603 A1 | 6/2014 | Sacha et al. |
| 2014/0177863 A1 | 6/2014 | Parkins |
| 2014/0254856 A1 | 9/2014 | Blick et al. |
| 2014/0275734 A1 | 9/2014 | Perkins et al. |
| 2014/0286514 A1 | 9/2014 | Pluvinage et al. |
| 2014/0288356 A1 | 9/2014 | Van |
| 2014/0288358 A1 | 9/2014 | Puria et al. |
| 2014/0296620 A1 | 10/2014 | Puria et al. |
| 2014/0321657 A1 | 10/2014 | Stirnemann |
| 2014/0379874 A1 | 12/2014 | Starr et al. |
| 2015/0021568 A1 | 1/2015 | Gong et al. |
| 2015/0023540 A1 | 1/2015 | Fay et al. |
| 2015/0031941 A1 | 1/2015 | Perkins et al. |
| 2015/0049889 A1 | 2/2015 | Bern |
| 2015/0117689 A1 | 4/2015 | Bergs et al. |
| 2015/0124985 A1 | 5/2015 | Kim et al. |
| 2015/0201269 A1 | 7/2015 | Dahl et al. |
| 2015/0222978 A1 | 8/2015 | Murozaki et al. |
| 2015/0245131 A1 | 8/2015 | Facteau et al. |
| 2015/0358743 A1 | 12/2015 | Killion |
| 2016/0008176 A1 | 1/2016 | Goldstein |
| 2016/0029132 A1 | 1/2016 | Freed et al. |
| 2016/0064814 A1 | 3/2016 | Jang et al. |
| 2016/0087687 A1 | 3/2016 | Kesler et al. |
| 2016/0094043 A1 | 3/2016 | Hao et al. |
| 2016/0150331 A1 | 5/2016 | Wenzel |
| 2016/0277854 A1 | 9/2016 | Puria et al. |
| 2016/0309265 A1 | 10/2016 | Pluvinage et al. |
| 2016/0309266 A1 | 10/2016 | Olsen et al. |
| 2016/0330555 A1 | 11/2016 | Vonlanthen et al. |
| 2017/0040012 A1 | 2/2017 | Goldstein |
| 2017/0095202 A1 | 4/2017 | Facteau et al. |
| 2017/0150275 A1 | 5/2017 | Puria et al. |
| 2017/0195801 A1 | 7/2017 | Rucker et al. |
| 2017/0195804 A1 | 7/2017 | Sandhu et al. |
| 2017/0195806 A1 | 7/2017 | Atamaniuk et al. |
| 2017/0195809 A1 | 7/2017 | Teran et al. |
| 2017/0257710 A1 | 9/2017 | Parker |
| 2018/0014128 A1 | 1/2018 | Puria et al. |
| 2018/0020291 A1 | 1/2018 | Puria et al. |
| 2018/0020296 A1 | 1/2018 | Wenzel |
| 2018/0077503 A1 | 3/2018 | Shaquer et al. |
| 2018/0077504 A1 | 3/2018 | Shaquer et al. |
| 2018/0167750 A1 | 6/2018 | Freed et al. |
| 2018/0213331 A1 | 7/2018 | Rucker et al. |
| 2018/0213335 A1 | 7/2018 | Puria et al. |
| 2018/0262846 A1 | 9/2018 | Perkins et al. |
| 2018/0317026 A1 | 11/2018 | Puria |
| 2018/0376255 A1 | 12/2018 | Parker |
| 2019/0069097 A1 | 2/2019 | Perkins et al. |
| 2019/0158961 A1 | 5/2019 | Puria et al. |
| 2019/0166438 A1 | 5/2019 | Perkins et al. |
| 2019/0230449 A1 | 7/2019 | Puria |
| 2019/0239005 A1 | 8/2019 | Sandhu et al. |
| 2019/0253811 A1 | 8/2019 | Unno et al. |
| 2019/0253815 A1 | 8/2019 | Atamaniuk et al. |
| 2020/0037082 A1 | 1/2020 | Perkins et al. |
| 2020/0068323 A1 | 2/2020 | Perkins et al. |
| 2020/0084551 A1 | 3/2020 | Puria et al. |
| 2020/0092662 A1 | 3/2020 | Wenzel |
| 2020/0092664 A1 | 3/2020 | Freed et al. |
| 2020/0128338 A1 | 4/2020 | Shaquer et al. |
| 2020/0186941 A1 | 6/2020 | Olsen et al. |
| 2020/0186942 A1 | 6/2020 | Flaherty et al. |
| 2020/0304927 A1 | 9/2020 | Shaquer et al. |
| 2020/0374639 A1 | 11/2020 | Rucker et al. |
| 2020/0396551 A1 | 12/2020 | Dy et al. |

(56) References Cited

U.S. PATENT DOCUMENTS

| | | | |
|---|---|---|---|
| 2021/0029451 A1 | 1/2021 | Fitz et al. | |
| 2021/0029474 A1 | 1/2021 | Larkin et al. | |

FOREIGN PATENT DOCUMENTS

| | | |
|---|---|---|
| CN | 1176731 A | 3/1998 |
| CN | 101459868 A | 6/2009 |
| CN | 105491496 A | 4/2016 |
| DE | 2044870 A1 | 3/1972 |
| DE | 3243850 A1 | 5/1984 |
| DE | 3508830 A1 | 9/1986 |
| EP | 0092822 A2 | 11/1983 |
| EP | 0242038 A2 | 10/1987 |
| EP | 0291325 A2 | 11/1988 |
| EP | 0296092 A2 | 12/1988 |
| EP | 0242038 A3 | 5/1989 |
| EP | 0296092 A3 | 8/1989 |
| EP | 0352954 A2 | 1/1990 |
| EP | 0291325 A3 | 6/1990 |
| EP | 0352954 A3 | 8/1991 |
| EP | 1035753 A1 | 9/2000 |
| EP | 1435757 A1 | 7/2004 |
| EP | 1845919 A1 | 10/2007 |
| EP | 1955407 A1 | 8/2008 |
| EP | 1845919 B1 | 9/2010 |
| EP | 2272520 A1 | 1/2011 |
| EP | 2301262 A1 | 3/2011 |
| EP | 2752030 A1 | 7/2014 |
| EP | 3101519 A1 | 12/2016 |
| EP | 2425502 B1 | 1/2017 |
| EP | 2907294 B1 | 5/2017 |
| EP | 3183814 A1 | 6/2017 |
| EP | 3094067 B1 | 10/2017 |
| EP | 3006079 B1 | 3/2019 |
| FR | 2455820 A1 | 11/1980 |
| GB | 2085694 A | 4/1982 |
| JP | S60154800 A | 8/1985 |
| JP | S621726 B2 | 1/1987 |
| JP | S63252174 A | 10/1988 |
| JP | S6443252 A | 2/1989 |
| JP | H09327098 A | 12/1997 |
| JP | 2000504913 A | 4/2000 |
| JP | 2004187953 A | 7/2004 |
| JP | 2004193908 A | 7/2004 |
| JP | 2005516505 A | 6/2005 |
| JP | 2006060833 A | 3/2006 |
| KR | 100624445 B1 | 9/2006 |
| WO | WO-9209181 A1 | 5/1992 |
| WO | WO-9501678 A1 | 1/1995 |
| WO | WO-9621334 A1 | 7/1996 |
| WO | WO-9736457 A1 | 10/1997 |
| WO | WO-9745074 A1 | 12/1997 |
| WO | WO-9806236 A1 | 2/1998 |
| WO | WO-9903146 A1 | 1/1999 |
| WO | WO-9915111 A1 | 4/1999 |
| WO | WO-0022875 A2 | 4/2000 |
| WO | WO-0022875 A3 | 7/2000 |
| WO | WO-0150815 A1 | 7/2001 |
| WO | WO-0158206 A2 | 8/2001 |
| WO | WO-0176059 A2 | 10/2001 |
| WO | WO-0158206 A3 | 2/2002 |
| WO | WO-0239874 A2 | 5/2002 |
| WO | WO-0239874 A3 | 2/2003 |
| WO | WO-03030772 A2 | 4/2003 |
| WO | WO-03063542 A2 | 7/2003 |
| WO | WO-03063542 A3 | 1/2004 |
| WO | WO-2004010733 A1 | 1/2004 |
| WO | WO-2005015952 A1 | 2/2005 |
| WO | WO-2005107320 A1 | 11/2005 |
| WO | WO-2006014915 A2 | 2/2006 |
| WO | WO-2006037156 A1 | 4/2006 |
| WO | WO-2006039146 A2 | 4/2006 |
| WO | WO-2006042298 A2 | 4/2006 |
| WO | WO-2006071210 A1 | 7/2006 |
| WO | WO-2006075169 A1 | 7/2006 |
| WO | WO-2006075175 A1 | 7/2006 |
| WO | WO-2006118819 A2 | 11/2006 |
| WO | WO-2006042298 A3 | 12/2006 |
| WO | WO-2007023164 A1 | 3/2007 |
| WO | WO-2009046329 A1 | 4/2009 |
| WO | WO-2009047370 A2 | 4/2009 |
| WO | WO-2009049320 A1 | 4/2009 |
| WO | WO-2009056167 A1 | 5/2009 |
| WO | WO-2009062142 A1 | 5/2009 |
| WO | WO-2009047370 A3 | 7/2009 |
| WO | WO-2009125903 A1 | 10/2009 |
| WO | WO-2009145842 A2 | 12/2009 |
| WO | WO-2009146151 A2 | 12/2009 |
| WO | WO-2009155358 A1 | 12/2009 |
| WO | WO-2009155361 A1 | 12/2009 |
| WO | WO-2009155385 A1 | 12/2009 |
| WO | WO-2010033932 A1 | 3/2010 |
| WO | WO-2010033933 A1 | 3/2010 |
| WO | WO-2010077781 A2 | 7/2010 |
| WO | WO-2010147935 A1 | 12/2010 |
| WO | WO-2010148345 A2 | 12/2010 |
| WO | WO-2011005500 A2 | 1/2011 |
| WO | WO-2012088187 A2 | 6/2012 |
| WO | WO-2012149970 A1 | 11/2012 |
| WO | WO-2013016336 A1 | 1/2013 |
| WO | WO-2016011044 A1 | 1/2016 |
| WO | WO-2016045709 A1 | 3/2016 |
| WO | WO-2016146487 A1 | 9/2016 |
| WO | WO-2017045700 A1 | 3/2017 |
| WO | WO-2017059218 A1 | 4/2017 |
| WO | WO-2017059240 A1 | 4/2017 |
| WO | WO-2017116791 A1 | 7/2017 |
| WO | WO-2017116865 A1 | 7/2017 |
| WO | WO-2018048794 A1 | 3/2018 |
| WO | WO-2018081121 A1 | 5/2018 |
| WO | WO-2018093733 A1 | 5/2018 |
| WO | WO-2019055308 A1 | 3/2019 |
| WO | WO-2019173470 A1 | 9/2019 |
| WO | WO-2019199680 A1 | 10/2019 |
| WO | WO-2019199683 A1 | 10/2019 |
| WO | WO-2020028082 A1 | 2/2020 |
| WO | WO-2020028083 A1 | 2/2020 |
| WO | WO-2020028084 A1 | 2/2020 |
| WO | WO-2020028085 A1 | 2/2020 |
| WO | WO-2020028086 A1 | 2/2020 |
| WO | WO-2020028087 A1 | 2/2020 |
| WO | WO-2020028088 A1 | 2/2020 |
| WO | WO-2020176086 A1 | 9/2020 |
| WO | WO-2021003087 A1 | 1/2021 |

OTHER PUBLICATIONS

Merriam-Webster's online dictionary definition of 'percutaneous'. Accessed on Jun. 3, 2013. 3 pages.

Edinger, J.R. High-Quality Audio Amplifier With Automatic Bias Control. Audio Engineering; Jun. 1947; pp. 7-9.

Hakansson, et al. Percutaneous vs. transcutaneous transducers for hearing by direct bone conduction (Abstract). Otolaryngol Head Neck Surg. Apr. 1990;102(4):339-44.

Mah. Fundamentals of photovoltaic materials. National Solar Power Research Institute. Dec. 21, 1998, 3-9.

Office action dated Apr. 17, 2018 for U.S. Appl. No. 15/282,570.

Robles, et al. Mechanics of the mammalian cochlea. Physiol Rev. Jul. 2001;81(3):1305-52.

U.S. Appl. No. 15/282,570 Notice of Allowance dated Jan. 17, 2019.

Web Books Publishing, "The Ear," accessed online Jan. 22, 2013, available online Nov. 2, 2007 at http://www.web-books.com/eLibrary/Medicine/Physiology/Ear/Ear.htm.

Wiki. Sliding Bias Variant 1, Dynamic Hearing (2015).

Asbeck, et al. Scaling Hard Vertical Surfaces with Compliant Microspine Arrays, The International Journal of Robotics Research 2006; 25; 1165-79.

Atasoy [Paper] Opto-acoustic Imaging. for BYM504E Biomedical Imaging Systems class at ITU, downloaded from the Internet www2.itu.edu.td—cilesiz/courses/BYM504- 2005-OA504041413. pdf, 14 pages.

(56) References Cited

OTHER PUBLICATIONS

Athanassiou, et al. Laser controlled photomechanical actuation of photochromic polymers Microsystems. Rev. Adv. Mater. Sci. 2003; 5:245-251.
Autumn, et al. Dynamics of geckos running vertically, The Journal of Experimental Biology 209, 260-272, (2006).
Autumn, et al., Evidence for van der Waals adhesion in gecko setae, www.pnas.orgcgiydoiy10.1073ypnas.192252799 (2002).
Ayatollahi, et al. Design and Modeling of Micromachined Condenser MEMS Loudspeaker using Permanent Magnet Neodymium-Iron-Boron (Nd—Fe—B). IEEE International Conference on Semiconductor Electronics, 2006. ICSSE '06, Oct. 29, 2006-Dec. 1, 2006; 160-166.
Baer, et al. Effects of Low Pass Filtering on the Intelligibility of Speech in Noise for People With and Without Dead Regions at High Frequencies. J. Acost. Soc. Am 112 (3), pt. 1, (Sep. 2002), pp. 1133-1144.
Best, et al. The influence of high frequencies on speech localization. Abstract 981 (Feb. 24, 2003) from www.aro.org/abstracts/abstracts.html.
Birch, et al. Microengineered systems for the hearing impaired. IEE Colloquium on Medical Applications of Microengineering, Jan. 31, 1996; pp. 2/1-2/5.
Boedts. Tympanic epithelial migration, Clinical Otolaryngology 1978, 3, 249-253.
Burkhard, et al. Anthropometric Manikin for Acoustic Research. J. Acoust. Soc. Am., vol. 58, No. 1, (Jul. 1975), pp. 214-222.
Camacho-Lopez, et al. Fast Liquid Crystal Elastomer Swims Into the Dark, Electronic Liquid Crystal Communications. Nov. 26, 2003; 9 pages total.
Carlile, et al. Frequency bandwidth and multi-talker environments. Audio Engineering Society Convention 120. Audio Engineering Society, May 20-23, 2006. Paris, France. 118:8 pages.
Carlile, et al. Spatialisation of talkers and the segregation of concurrent speech. Abstract 1264 (Feb. 24, 2004) from www.aro.org/abstracts/abstracts.html.
Cheng; et al., "A silicon microspeaker for hearing instruments. Journal of Micromechanics and Microengineering 14, No. 7 (2004): 859-866.".
Cheng, et al. A Silicon Microspeaker for Hearing Instruments. Journal of Micromechanics and Microengineering 2004; 14(7):859-866.
Datskos, et al. Photoinduced and thermal stress in silicon microcantilevers. Applied Physics Letters. Oct. 19, 1998; 73(16):2319-2321.
Decraemer, et al. A method for determining three-dimensional vibration in the ear. Hearing Res., 77:19-37 (1994).
Dundas et al. The Earlens Light-Driven Hearing Aid: Top 10 questions and answers. Hearing Review. 2018;25(2):36-39.
Ear. Downloaded from the Internet. Accessed Jun. 17, 2008. 4 pages. URL:<http://wwwmgs.bionet.nsc.ru/mgs/gnw/trrd/thesaurus/Se/ear.html>.
Fay. Cat eardrum mechanics. Ph.D. thesis. Disseration submitted to Department of Aeronautics and Astronautics. Standford University. May 2001; 210 pages total.
Fay, et al. Cat eardrum response mechanics. Mechanics and Computation Division. Department of Mechanical Engineering. Stanford University. 2002; 10 pages total.
Fay, et al. Preliminary evaluation of a light-based contact hearing device for the hearing impaired. Otol Neurotol. Jul. 2013;34(5):912-21. doi: 10.1097/MAO.0b013e31827de4b1.
Fay, et al. The discordant eardrum, PNAS, Dec. 26, 2006, vol. 103, No. 52, p. 19743-19748.
Fletcher. Effects of Distortion on the Individual Speech Sounds. Chapter 18, ASA Edition of Speech and Hearing in Communication, Acoust Soc.of Am. (republished in 1995) pp. 415-423.
Freyman, et al. Spatial Release from Informational Masking in Speech Recognition. J. Acost. Soc. Am., vol. 109, No. 5, pt. 1, (May 2001); 2112-2122.
Freyman, et al. The Role of Perceived Spatial Separation in the Unmasking of Speech. J. Acoust. Soc. Am., vol. 106, No. 6, (Dec. 1999); 3578-3588.
Fritsch, et al. EarLens transducer behavior in high-field strength MRI scanners. Otolaryngol Head Neck Surg. Mar. 2009;140(3):426-8. doi: 10.1016/j.otohns.2008.10.016.
Galbraith et al. A wide-band efficient inductive transdermal power and data link with coupling insensitive gain IEEE Trans Biomed Eng. Apr. 1987;34(4):265-75.
Gantz, et al. Broad Spectrum Amplification with a Light Driven Hearing System. Combined Otolaryngology Spring Meetings, 2016 (Chicago).
Gantz, et al. Light Driven Hearing Aid: A Multi-Center Clinical Study. Association for Research in Otolaryngology Annual Meeting, 2016 (San Diego).
Gantz, et al. Light-Driven Contact Hearing Aid for Broad Spectrum Amplification: Safety and Effectiveness Pivotal Study. Otology & Neurotology Journal, 2016 (in review).
Gantz, et al. Light-Driven Contact Hearing Aid for Broad-Spectrum Amplification: Safety and Effectiveness Pivotal Study. Otology & Neurotology. Copyright 2016. 7 pages.
Ge, et al., Carbon nanotube-based synthetic gecko tapes, p. 10792-10795, PNAS, Jun. 26, 2007, vol. 104, No. 26.
Gennum, GA3280 Preliminary Data Sheet: Voyageur TD Open Platform DSP System for Ultra Low Audio Processing, downloaded from the Internet:<<http://www.sounddesigntechnologies.com/products/pdf/37601DOC.pdf>>, Oct. 2006; 17 pages.
Gobin, et al. Comments on the physical basis of the active materials concept. Proc. SPIE 2003; 4512:84-92.
Gorb, et al. Structural Design and Biomechanics of Friction-Based Releasable Attachment Devices in Insects, INTEGR. COMP_ BIOL., 42:1127-1139 (2002).
Hato, et al. Three-dimensional stapes footplate motion in human temporal bones. Audiol. Neurootol., 8:140-152 (Jan. 30, 2003).
Headphones. Wikipedia Entry. Downloaded from the Internet. Accessed Oct. 27, 2008. 7 pages. URL: http://en.wikipedia.org/wiki/Headphones>.
Hofman, et al. Relearning Sound Localization With New Ears. Nature Neuroscience, vol. 1, No. 5, (Sep. 1998); 417-421.
International Search Report and Written Opinion dated Dec. 13, 2016 for International PCT Patent Application No. PCT/US2016/054714.
Izzo, et al. Laser Stimulation of Auditory Neurons: Effect of Shorter Pulse Duration and Penetration Depth. Biophys J. Apr. 15, 2008;94(8):3159-3166.
Izzo, et al. Laser Stimulation of the Auditory Nerve. Lasers Surg Med. Sep. 2006;38(8):745-753.
Izzo, et al. Selectivity of Neural Stimulation in the Auditory System: A Comparison of Optic and Electric Stimuli. J Biomed Opt. Mar.-Apr. 2007;12(2):021008.
Jian, et al. A 0.6 V, 1.66 mW energy harvester and audio driver for tympanic membrane transducer with wirelessly optical signal and power transfer. InCircuits and Systems (ISCAS), 2014 IEEE International Symposium on Jun. 1, 2014. 874-7. IEEE.
Jin, et al. Speech Localization. J. Audio Eng. Soc. convention paper, presented at the AES 112th Convention, Munich, Germany, May 10-13, 2002, 13 pages total.
Khaleghi, et al. Attenuating the ear canal feedback pressure of a laser-driven hearing aid. J Acoust Soc Am. Mar. 2017;141(3):1683.
Khaleghi et al. Attenuating the feedback pressure of a light-activated hearing device to allows microphone placement at the ear canal entrance. IHCON 2016, International Hearing Aid Research Conference, Tahoe City, CA, Aug. 2016.
Khaleghi, et al. Characterization of Ear-Canal Feedback Pressure due to Umbo-Drive Forces: Finite-Element vs. Circuit Models. ARO Midwinter Meeting 2016, (San Diego).
Khaleghi et al. Mechano-Electro-Magnetic Finite Element Model of a Balanced Armature Transducer for a Contact Hearing Aid. Proc. MoH 2017, Mechanics of Hearing workshop, Brock University, Jun. 2017.
Khaleghi et al. Multiphysics Finite Element Model of a Balanced Armature Transducer used in a Contact Hearing Device. ARO 2017, 40th ARO MidWinter Meeting, Baltimore, MD, Feb. 2017.

(56) References Cited

OTHER PUBLICATIONS

Kiessling, et al. Occlusion Effect of Earmolds with Different Venting Systems. J Am Acad Audiol. Apr. 2005;16(4):237-49.
Killion, et al. The case of the missing dots: AI and SNR loss. The Hearing Journal, 1998. 51(5), 32-47.
Killion. Myths About Hearing Noise and Directional Microphones. The Hearing Review. Feb. 2004; 11(2):14, 16, 18, 19, 72 & 73.
Killion. SNR loss: I can hear what people say but I can't understand them. The Hearing Review, 1997; 4(12):8-14.
Lee, et al. A Novel Opto-Electromagnetic Actuator Coupled to the tympanic Membrane. J Biomech. Dec. 5, 2008;41(16):3515-8. Epub Nov. 7, 2008.
Lee, et al. The optimal magnetic force for a novel actuator coupled to the tympanic membrane: a finite element analysis. Biomedical engineering: applications, basis and communications. 2007; 19(3):171-177.
Levy, et al. Characterization of the available feedback gain margin at two device microphone locations, in the fossa triangularis and Behind the Ear, for the light-based contact hearing device. Acoustical Society of America (ASA) meeting, 2013 (San Francisco).
Levy, et al. Extended High-Frequency Bandwidth Improves Speech Reception in the Presence of Spatially Separated Masking Speech. Ear Hear. Sep.-Oct. 2015;36(5):e214-24. doi: 10.1097/AUD.0000000000000161.
Levy et al. Light-driven contact hearing aid: a removable direct-drive hearing device option for mild to severe sensorineural hearing impairment. Conference on Implantable Auditory Prostheses, Tahoe City, CA, Jul. 2017. 4 pages.
Lezal. Chalcogenide glasses—survey and progress. Journal of Optoelectronics and Advanced Materials. Mar. 2003; 5(1):23-34.
Makino, et al. Epithelial migration in the healing process of tympanic membrane perforations. Eur Arch Otorhinolaryngol. 1990; 247: 352-355.
Makino, et al., Epithelial migration on the tympanic membrane and external canal, Arch Otorhinolaryngol (1986) 243:39-42.
Markoff. Intuition + Money: An Aha Moment. New York Times Oct. 11, 2008, p. BU4, 3 pages total.
Martin, et al. Utility of Monaural Spectral Cues is Enhanced in the Presence of Cues to Sound-Source Lateral Angle. JARO. 2004; 5:80-89.
McElveen et al. Overcoming High-Frequency Limitations of Air Conduction Hearing Devices Using a Light-Driven Contact Hearing Aid. Poster presentation at The Triological Society, 120th Annual Meeting at COSM, Apr. 28, 2017; San Diego, CA.
Michaels, et al., Auditory Epithelial Migration on the Human Tympanic Membrane: II. The Existence of Two Discrete Migratory Pathways and Their Embryologic Correlates, The American Journal of Anatomy 189:189-200 (1990).
Moore, et al. Perceived naturalness of spectrally distorted speech and music. J Acoust Soc Am. Jul. 2003;114(1):408-19.
Moore, et al. Spectro-temporal characteristics of speech at high frequencies, and the potential for restoration of audibility to people with mild-to-moderate hearing loss. Ear Hear. Dec. 2008;29(6):907-22. doi: 10.1097/AUD.0b013e31818246f6.
Moore. Loudness perception and intensity resolution. Cochlear Hearing Loss, Chapter 4, pp. 90-115, Whurr Publishers Ltd., London (1998).
Murphy M, Aksak B, Sitti M. Adhesion and anisotropic friction enhancements of angled heterogeneous micro-fiber arrays with spherical and spatula tips. J Adhesion Sci Technol, vol. 21, No. 12-13, p. 1281-1296, 2007.
Murugasu, et al. Malleus-to-footplate versus malleus-to-stapes-head ossicular reconstruction prostheses: temporal bone pressure gain measurements and clinical audiological data. Otol Neurotol. Jul. 2005; 2694):572-582.
Musicant, et al. Direction-Dependent Spectral Properties of Cat External Ear: New Data and Cross-Species Comparisons. J. Acostic. Soc. Am, May 10-13, 2002, vol. 87, No. 2, (Feb. 1990), pp. 757-781.

National Semiconductor, LM4673 Boomer: Filterless, 2.65W, Mono, Class D Audio Power Amplifier, [Data Sheet] downloaded from the Internet:<<http://www.national.com/ds/LM/LM4673.pdf>>; Nov. 1, 2007; 24 pages.
Nishihara, et al. Effect of changes in mass on middle ear function. Otolaryngol Head Neck Surg. Nov. 1993;109(5):889-910.
O'Connor, et al. Middle ear Cavity and Ear Canal Pressure-Driven Stapes Velocity Responses in Human Cadaveric Temporal Bones. J Acoust Soc Am. Sep. 2006;120(3):1517-28.
Park, et al. Design and analysis of a microelectromagnetic vibration transducer used as an implantable middle ear hearing aid. J. Micromech. Microeng. vol. 12 (2002), pp. 505-511.
Perkins, et al. Light-based Contact Hearing Device: Characterization of available Feedback Gain Margin at two device microphone locations. Presented at AAO-HNSF Annual Meeting, 2013 (Vancouver).
Perkins, et al. The EarLens Photonic Transducer: Extended bandwidth. Presented at AAO-HNSF Annual Meeting, 2011 (San Francisco).
Perkins, et al. The EarLens System: New sound transduction methods. Hear Res. Feb. 2, 2010; 10 pages total.
Perkins, R. Earlens tympanic contact transducer: a new method of sound transduction to the human ear. Otolaryngol Head Neck Surg. Jun. 1996;114(6):720-8.
Poosanaas, et al. Influence of sample thickness on the performance of photostrictive ceramics, J. App. Phys. Aug. 1, 1998; 84(3):1508-1512.
Puria et al. A gear in the middle ear. ARO Denver CO, 2007b.
Puria, et al. Cues above 4 kilohertz can improve spatially separated speech recognition. The Journal of the Acoustical Society of America, 2011, 129, 2384.
Puria, et al. Extending bandwidth above 4 kHz improves speech understanding in the presence of masking speech. Association for Research in Otolaryngology Annual Meeting, 2012 (San Diego).
Puria, et al. Extending bandwidth provides the brain what it needs to improve hearing in noise. First international conference on cognitive hearing science for communication, 2011 (Linkoping, Sweden).
Puria, et al. Hearing Restoration: Improved Multi-talker Speech Understanding. 5th International Symposium on Middle Ear Mechanics in Research and Otology (MEMRO), Jun. 2009 (Stanford University).
Puria, et al. Imaging, Physiology and Biomechanics of the middle ear: Towards understating the functional consequences of anatomy. Stanford Mechanics and Computation Symposium, 2005, ed Fong J.
Puria, et al. Malleus-to-footplate ossicular reconstruction prosthesis positioning: cochleovestibular pressure optimization. Otol Nerotol. May 2005; 2693):368-379.
Puria, et al. Measurements and model of the cat middle ear: Evidence of tympanic membrane acoustic delay. J. Acoust. Soc. Am., 104(6):3463-3481 (Dec. 1998).
Puria, et al., Mechano-Acoustical Transformations in A. Basbaum et al., eds., The Senses: A Comprehensive Reference, v3, p. 165-202, Academic Press (2008).
Puria, et al. Middle Ear Morphometry From Cadaveric Temporal Bone MicroCT Imaging. Proceedings of the 4th International Symposium, Zurich, Switzerland, Jul. 27-30, 2006, Middle Ear Mechanics in Research and Otology, pp. 259-268.
Puria, et al. Sound-Pressure Measurements in the Cochlear Vestibule of Human-Cadaver Ears. Journal of the Acoustical Society of America. 1997; 101 (5-1): 2754-2770.
Puria, et al. Temporal-Bone Measurements of the Maximum Equivalent Pressure Output and Maximum Stable Gain of a Light-Driven Hearing System That Mechanically Stimulates the Umbo. Otol Neurotol. Feb. 2016;37(2):160-6. doi: 10.1097/MAO.0000000000000941.
Puria, et al. The EarLens Photonic Hearing Aid. Association for Research in Otolaryngology Annual Meeting, 2012 (San Diego).
Puria, et al. The Effects of bandwidth and microphone location on understanding of masked speech by normal-hearing and hearing-impaired listeners. International Conference for Hearing Aid Research (IHCON) meeting, 2012 (Tahoe City).

(56) References Cited

OTHER PUBLICATIONS

Puria, et al. Tympanic-membrane and malleus-incus-complex co-adaptations for high-frequency hearing in mammals. Hear Res. May 2010;263(1-2):183-90. doi: 10.1016/j.heares.2009.10.013. Epub Oct. 28, 2009.
Puria. Measurements of human middle ear forward and reverse acoustics: implications for otoacoustic emissions. J Acoust Soc Am. May 2003;113(5):2773-89.
Puria, S. Middle Ear Hearing Devices. Chapter 10. Part of the series Springer Handbook of Auditory Research pp. 273-308. Date: Feb. 9, 2013.
Qu, et al. Carbon Nanotube Arrays with Strong Shear Binding-On and Easy Normal Lifting-Off, Oct. 10, 2008 vol. 322 Science. 238-242.
Roush. SiOnyx Brings "Black Silicon" into the Light; Material Could Upend Solar, Imaging Industries. Xconomy, Oct. 12, 2008, retrieved from the Internet: www.xconomy.com/boston/2008/10/12/sionyx-brings-black-silicon-into-the-light-material-could-upend-solar-imaging-industries> 4 pages total.
R.P. Jackson, C. Chlebicki, T.B. Krasieva, R. Zalpuri, W.J. Triffo, S. Puria, "Multiphoton and Transmission Electron Microscopy of Collagen in Ex Vivo Tympanic Membranes," Biomedcal Computation at STandford, Oct. 2008.
Rubinstein. How Cochlear Implants Encode Speech, Curr Opin Otolaryngol Head Neck Surg. Oct. 2004;12(5):444-8; retrieved from the Internet: www.ohsu.edu/nod/documents/week3/Rubenstein.pdf.
School of Physics Sydney, Australia. Acoustic Compliance, Inertance and Impedance. 1-6. (2018). http://www.animations.physics.unsw.edu.au/w/compliance-inertance-impedance.htm.
Sekaric, et al. Nanomechanical resonant structures as tunable passive modulators. App. Phys. Lett. Nov. 2003; 80(19):3617-3619.
Shaw. Transformation of Sound Pressure Level From the Free Field to the Eardrum in the Horizontal Plane. J. Acoust. Soc. Am., vol. 56, No. 6, (Dec. 1974), 1848-1861.
Shih. Shape and displacement control of beams with various boundary conditions via photostrictive optical actuators. Proc. IMECE. Nov. 2003; 1-10.
Song, et al. The development of a non-surgical direct drive hearing device with a wireless actuator coupled to the tympanic membrane. Applied Acoustics. Dec. 31, 2013;74(12):1511-8.
Sound Design Technologies,—Voyager TDTM Open Platform DSP System for Ultra Low Power Audio Processing—GA3280 Data Sheet. Oct. 2007; retrieved from the Internet:<<http://www.sounddes.com/pdf/37601DOC.pdf>>, 15 page total.
Wikipedia. Inductive Coupling. 1-2 (Jan. 11, 2018) https://en.wikipedia.org/wiki/Inductive_coupling.
Wikipedia. Pulse-density Coupling. 1-4 (Apr. 6, 2017). https://en.wikipedia.org/wiki/Pulse-density_modulation.
Spolenak, et al. Effects of contact shape on the scaling of biological attachments. Proc. R. Soc. A. 2005; 461:305-319.
Stenfelt, et al. Bone-Conducted Sound: Physiological and Clinical Aspects. Otology & Neurotology, Nov. 2005; 26 (6):1245-1261.
Struck, et al. Comparison of Real-world Bandwidth in Hearing Aids vs Earlens Light-driven Hearing Aid System. The Hearing Review. TechTopic: EarLens. Hearingreview.com. Mar. 14, 2017. pp. 24-28.
Stuchlik, et al. Micro-Nano Actuators Driven by Polarized Light. IEEE Proc. Sci. Meas. Techn. Mar. 2004; 151(2):131-136.
Suski, et al. Optically activated ZnO/SiO2/Si cantilever beams. Sensors and Actuators A (Physical), 0 (nr: 24). 2003; 221-225.
Takagi, et al. Mechanochemical Synthesis of Piezoelectric PLZT Powder. KONA. 2003; 51(21):234-241.
Thakoor, et al. Optical microactuation in piezoceramics. Proc. SPIE. Jul. 1998; 3328:376-391.
The Scientist and Engineers Guide to Digital Signal Processing, copyright 01997-1998 by Steven W. Smith, available online at www.DSPguide.com.
Thompson. Tutorial on microphone technologies for directional hearing aids. Hearing Journal. Nov. 2003; 56(11):14-16,18, 20-21.
Tzou, et al. Smart Materials, Precision Sensors/Actuators, Smart Structures, and Structronic Systems. Mechanics of Advanced Materials and Structures. 2004; 11:367-393.
Uchino, et al. Photostricitve actuators. Ferroelectrics. 2001; 258:147-158.
Vickers, et al. Effects of Low-Pass Filtering on the Intelligibility of Speech in Quiet for People With and Without Dead Regions at High Frequencies. J. Acoust. Soc. Am. Aug. 2001; 110(2):1164-1175.
Vinge. Wireless Energy Transfer by Resonant Inductive Coupling. Master of Science Thesis. Chalmers University of Technology. 1-83 (2015).
Vinikman-Pinhasi, et al. Piezoelectric and Piezooptic Effects in Porous Silicon. Applied Physics Letters, Mar. 2006; 88(11): 11905-111906.
Wang, et al. Preliminary Assessment of Remote Photoelectric Excitation of an Actuator for a Hearing Implant. Proceeding of the 2005 IEEE, Engineering in Medicine and Biology 27th nnual Conference, Shanghai, China. Sep. 1-4, 2005; 6233-6234.
Wiener, et al. On the Sound Pressure Transformation by the Head and Auditory Meatus of the Cat. Acta Otolaryngol. Mar. 1966; 61(3):255-269.
Wightman, et al. Monaural Sound Localization Revisited. J Acoust Soc Am. Feb. 1997;101(2):1050-1063.
Wikipedia. Resonant Inductive Coupling. 1-11 (Jan. 12, 2018). https://en.wikipedia.org/wiki/Resonant_inductive_couping#cite_note-13.
Yao, et al. Adhesion and sliding response of a biologically inspired fibrillar surface: experimental observations, J. R. Soc. Interface (2008) 5, 723-733 doi:10.1098/rsif.2007.1225 Published online Oct. 30, 2007.
Yao, et al. Maximum strength for intermolecular adhesion of nanospheres at an optimal size. J. R. Soc. Interface doi:10.10981rsif.2008.0066 Published online 2008.
Yi, et al. Piezoelectric Microspeaker with Compressive Nitride Diaphragm. The Fifteenth IEEE International Conference on Micro Electro Mechanical Systems, 2002; 260-263.
Yu, et al. Photomechanics: Directed bending of a polymer film by light. Nature. Sep. 2003; 425:145.
Co-pending U.S. Appl. No. 17/066,341, inventors Larkin; Brendan et al., filed Oct. 8, 2020.
Co-pending U.S. Appl. No. 17/066,345, inventors Fitz, Kelly et al., filed Oct. 8, 2020.
Knight, D. Diode detectors for RF measurement. Paper. Jan. 1, 2016. [Retrieved from 1-16 online] (retrieved Feb. 11, 2020) abstract, p. 1; section 1, p. 6; section 1.3, p. 9; section 3 voltage-double rectifier, p. 21; section 5, p. 27. URL: g3ynh.info/circuits/Diode_det.pdf.
U.S. Appl. No. 15/282,570 Notice of Allowance dated Feb. 28, 2019.

WEARABLE CUSTOMIZED EAR CANAL APPARATUS

CROSS REFERENCE TO RELATED APPLICATIONS

This application is a continuation of U.S. patent application Ser. No. 15/282,570, filed Sep. 30, 2016, now U.S. Pat. No. 10,292,601, which claims the benefit of U.S. Provisional Application Nos. 62/236,295, filed Oct. 2, 2015, and 62/395,667, filed Sep. 16, 2016, the entirety of which are incorporated herein by reference.

BACKGROUND OF THE INVENTION

The present invention is related to wearable devices and methods for their use. The present invention is further related to hearing devices. The present invention is further related to methods for the use of wearable devices and hearing devices.

SUMMARY OF THE INVENTION

The present invention is directed to a wearable system wherein elements of the system, including various sensors, are adapted to detect biometric and other data and/or to deliver drugs. In this invention, the elements of the system are positioned proximal to, on, or in the ear canal of a person. In embodiments of the invention, elements of the system are positioned external to, on or in the ear canal and may reside there for extended periods of time. For example, an element of the system may be positioned on the tympanic membrane of a user and left there overnight, for multiple days, months or years. Because of the position and longevity of the system elements in the ear canal, the present invention has many advantages over prior wearable biometric devices.

BRIEF DESCRIPTION OF THE DRAWINGS

The foregoing and other objects, features and advantages of embodiments of the present inventive concepts will be apparent from the more particular description of preferred embodiments, as illustrated in the accompanying drawings in which like reference characters refer to the same or like elements. The drawings are not necessarily to scale; emphasis instead being placed upon illustrating the principles of the preferred embodiments.

DETAILED DESCRIPTION OF THE INVENTION

Figure 1:
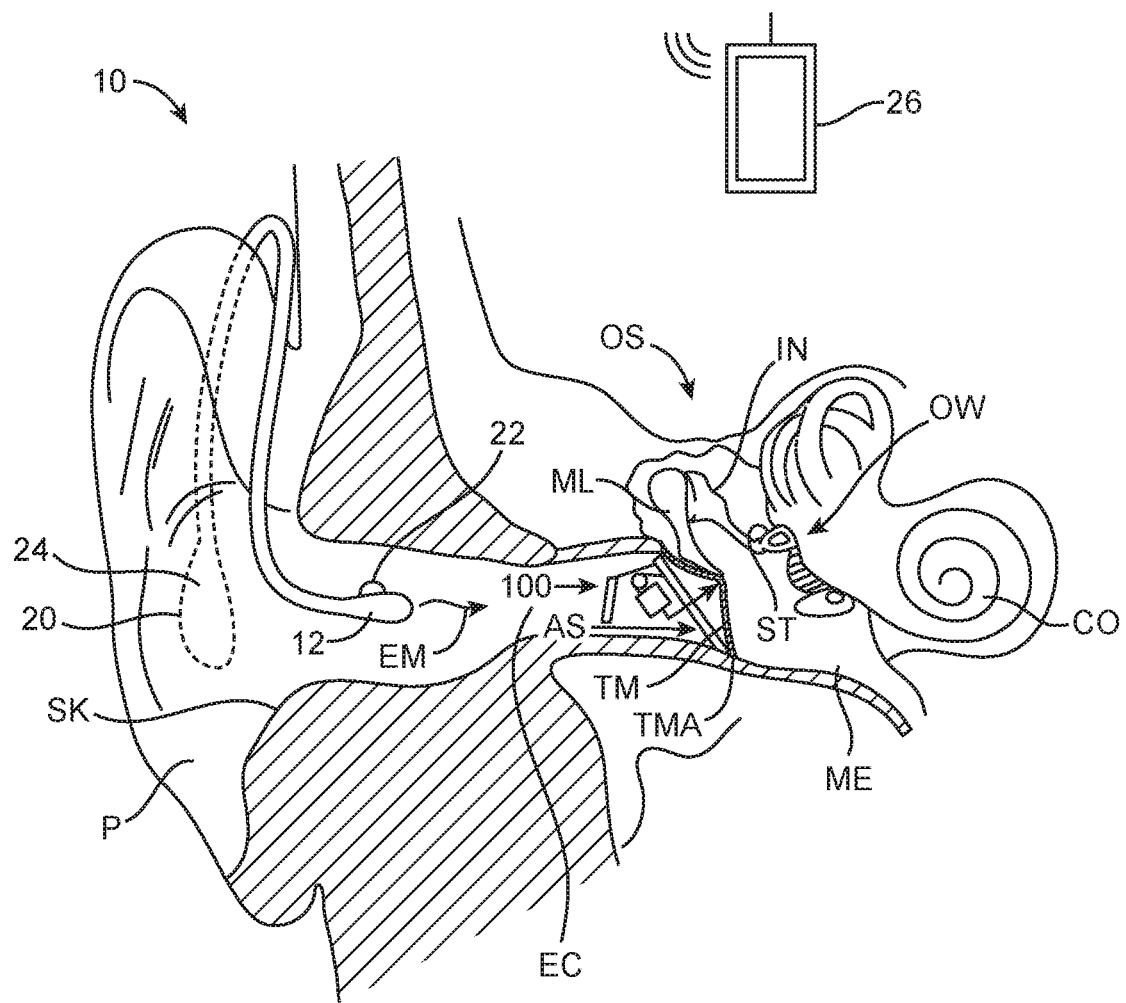
FIG. 1 shows a hearing system configured in accordance with embodiments of the present invention.

In embodiments of the present invention, biometric sensors and other devices may be placed in proximity to, on or in the ear canal resulting in a system with the ability to collect information on the user's environment, including information on the user's location, the time of day, and the activity the user is engaged in. In embodiments of the present invention, drug delivery devices may be placed in proximity to, on or in the ear canal resulting in a system with the ability to deliver drugs to a user through the ear and/or components of the ear. In embodiments of the present invention, the combination of a superior hearing system with biometric sensors and other devices, such as drug delivery devices, in a single system which may be placed in proximity to, on or in the ear canal may result in a system with the ability to collect information on the user's environment, including information on the user's location, the time of day, and the activity the user is engaged in. The system may further provide access to highly vascular sections of ear canal, including the pars tensa and manubrium vessels and the information that may be gathered from such locations. The system may further provide the ability to gather data, monitor health, send alerts and deliver drugs through a device that is in place 24 hours a day for years on end, without interfering with or changing the wearer's day to day activities. The system may further provide the ability to ensure user compliance without the need for user interaction, other than, in some cases, normal upkeep. In some embodiments, the current invention may be used to replace halter monitors, event recorders and/or Sub-Cutaneous (Sub-Q) monitors (e.g. injectable monitors). The system may further provide the ability to mount sensors directly against the skin and ensure that they stay in place over long periods of time, by, for example, using system components that are custom fit to the ear canal wall and/or to the tympanic membrane. The system may further provide the user with feedback, instructions or warnings which go directly to the wearer's tympanic membrane in a manner which is imperceptible to any third party.

A system according to the present invention may further enable a user to take advantage of characteristics of the ear canal of the user to make measurements of the user's biometric data, including: positioning of sensors in a place, which is undetectable to both the user and third parties; positioning of sensors in a place where they are well protected from the environment, and from external forces (not subject to false alarms, such as, for example, the type of false alarms that result from the dropping or shaking of externally worn devices); positioning of sensors in a very vascular environment; positioning sensors in an environment which may be highly conducive to the measurement of biometric data (an environment where a better signal to noise ratio is achievable—enclosed and dark to facilitate optical measurements; and positioning sensors in an environment where an extensive range of biometric data is available and can be measured, including blood pressure, heart rate, glucose levels, respiration rate, temperature, blood flow and other biometric data.

A system according to the present invention may further provide: the ability to deliver drugs to a user, including sustained, timed and/or algorithm controlled drug delivery; the ability to ensure compliance with drug regimens by automating drug delivery in an easily accessible region such as the ear canal; the ability to limit the amount of drug delivered without compromising efficacy by delivering to highly vascular tissue in or around the ear canal, such as, for example, the pars tensa and manubrium vessels; the ability to deliver drugs to regions of the body where the vasculature is easily accessible, for example, where the tissue covering the vasculature is very thin, such as, for example, over the manubrium vessels; the ability to locally deliver drugs which are normally delivered systemically, thereby reducing the amount of drugs delivered and the related side effects; and the ability to deliver drugs and treat diseases using a novel platform in the ear canal. Drugs which may be delivered using the present invention include antibiotics (neomycin/quinolenes), dexamethasone, steroids (prednisolone), acetic acid, aluminum acetate, boric acid, betnesol, prednisolone sodium phosphate, clotrimazole, Ceruminolytic agents (sodium chloride/chlorbutanol/paradichlorobenzene), amoxicillin, flucloxacillin; ciprofloxacillin, penicillin, betahistine dopamine antagonists (prochlorperazine), antihistamines (cinnarizine and cyclizine), antiviral drugs (acyclovir), sodium fluoride, nicotine and insulin. Diseases which may be treated using the present invention include acute otitis media, furunculosis of external auditory canal, perichondritis of pinna, acute mastoiditis, and malignant otitis externa, vertigo, herpes zoster oticus and cancer. Embodiments of the invention may be used to deliver drugs in which systemic or local drug delivery would be beneficial.

FIG. 1 shows a hearing system 10 configured to transmit electromagnetic energy EM to a medial ear canal assembly 100 positioned in the ear canal EC of the user. The ear comprises an external ear, a middle ear ME and an inner ear. The external ear comprises a Pinna P and an ear canal EC and is bounded medially by a tympanic membrane (also referred to as an eardrum) TM. Ear canal EC extends medially from pinna P to tympanic membrane TM. Ear canal EC is at least partially defined by a skin SK disposed along the surface of the ear canal. The tympanic membrane TM comprises a tympanic membrane annulus TMA that extends circumferentially around a majority of the eardrum to hold the eardrum in place. The middle ear ME is disposed between tympanic membrane TM of the ear and a cochlea CO of the ear. The middle ear ME comprises the ossicles OS to couple the tympanic membrane TM to cochlea CO. The ossicles OS comprise an incus IN, a malleus ML and a stapes ST. The malleus ML is connected to the tympanic membrane TM and the stapes ST is connected to an oval window OW, with the incus IN disposed between the malleus ML and stapes ST. Stapes ST is coupled to the oval window OW so as to conduct sound from the middle ear to the cochlea.

The hearing system 10 may include an input transducer assembly 20 and a medial ear canal assembly 100 to transmit sound to the user. Hearing system 10 may comprise a sound processor 24, which may be, for example, a behind the ear unit (BTE). Sound processor 24 may comprise many components of hearing system 10 such as a speech processor, battery, wireless transmission circuitry, and input transducer assembly 20. The input transducer assembly 20 can be located at least partially behind the pinna P or substantially or entirely within the ear canal EC. Input transducer assembly 20 may further comprise a Bluetooth™ connection to couple to a cell phone or other external communication device 26. The medial ear canal assembly 100 of hearing system 10 may comprise components to receive the light energy or other energy, such as RF energy and vibrate the eardrum in response to such energy.

The input transducer assembly 20 can receive a sound input, for example an audio sound or an input from external communication device 26. With hearing aids for hearing impaired individuals, the input can be ambient sound. The input transducer assembly may comprise at least one input transducer, for example a microphone 22. The at least one input transducer may comprise a second microphone located away from the first microphone, in the ear canal or the ear canal opening, for example positioned on sound processor 24. Input transducer assembly 20 may also include can include a suitable amplifier or other electronic interface. In some embodiments, the input may comprise an electronic sound signal from a sound producing or receiving device, such as a telephone, a cellular telephone, a Bluetooth connection, a radio, a digital audio unit, and the like.

Input transducer assembly 20 may include a lateral ear canal assembly 12 which may comprise a light source such as an LED or a laser diode for transmitting data (including audio data) and energy to medial ear canal assembly 100. In other embodiments, lateral ear canal assembly 12 may comprise an electromagnetic coil, an RF source, or the like for transmitting data (including audio data) and energy to medial ear canal assembly 100. In embodiments of the invention, lateral ear canal assembly 12 may further comprise a receiver adapted to receive data transmitted from medial ear canal assembly 100, such as, for example, biometric data from sensors positioned on or near medial ear canal assembly 100.

In embodiments of the invention, medial ear canal assembly 100 is adapted to receive the output from input transducer assembly 20 and produce mechanical vibrations in response to the received information, which may be, for example, in the form of a light signal generated by lateral ear canal assembly 12. In embodiments of the invention, medial ear canal assembly 100 comprises a sound transducer, wherein the sound transducer may comprise at least one of a microactuator, a coil, a magnet, a magnetostrictive element, a photostrictive element, or a piezoelectric element. In embodiments of the invention, input transducer assembly 20 may comprise a light source coupled to sound processor 24 by a fiber optic cable and positioned on lateral ear canal assembly 12. In embodiments of the invention, input transducer assembly 20 may comprise a laser diode coupled to sound processor 24 and positioned on lateral ear canal assembly 12. In embodiments of the invention, the light source of the input transducer assembly 20 may be positioned in the ear canal along with sound processor 24 and microphone 22. When properly coupled to the subject's hearing transduction pathway, the mechanical vibrations caused by medial ear canal assembly 100 can stimulate the cochlea CO, which induces neural impulses in the subject which can be interpreted by the subject as a sound input.

Figure 2:
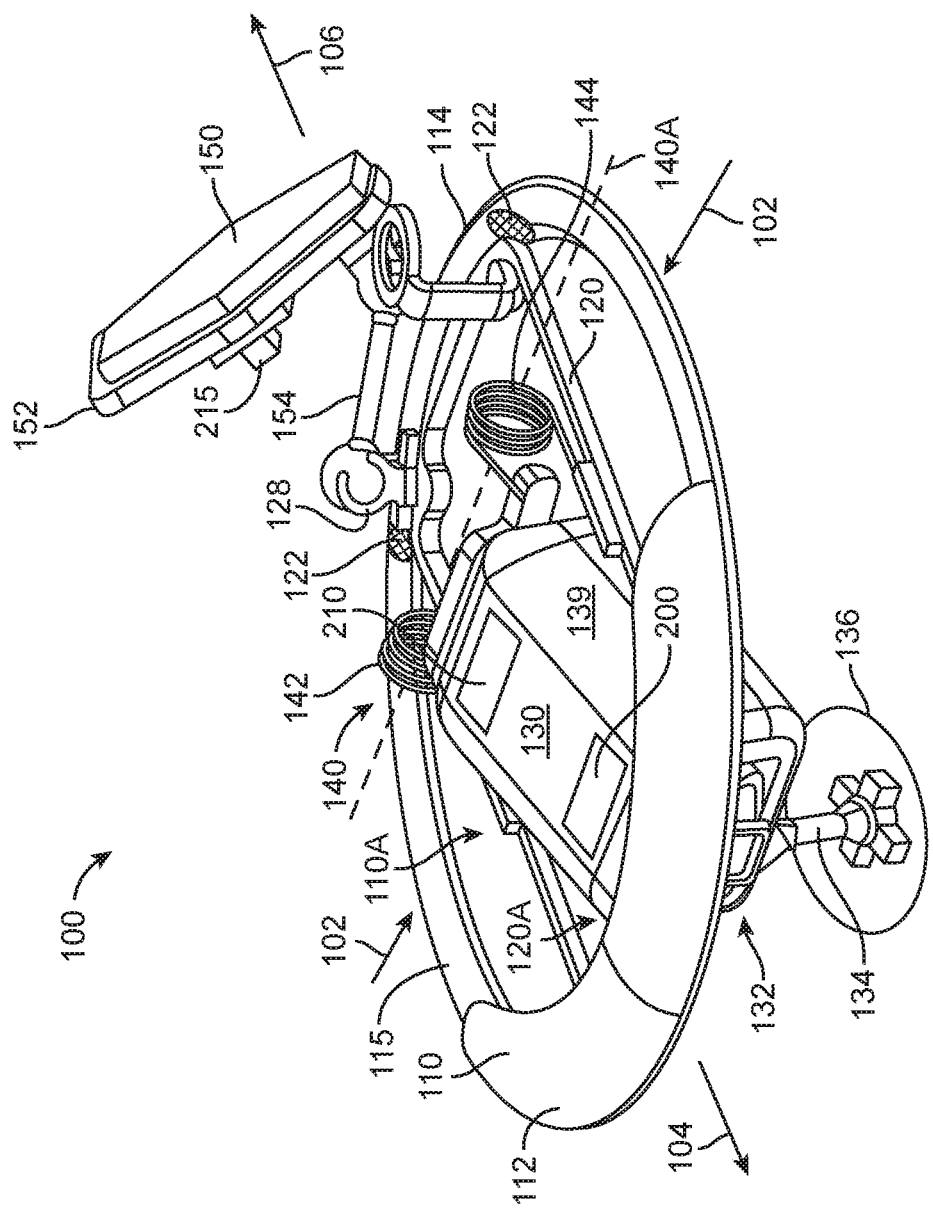
FIG. 2 shows an isometric view of the medial ear canal assembly of the hearing system of FIG. 1 in accordance with embodiments of the present invention.
Figure 3:
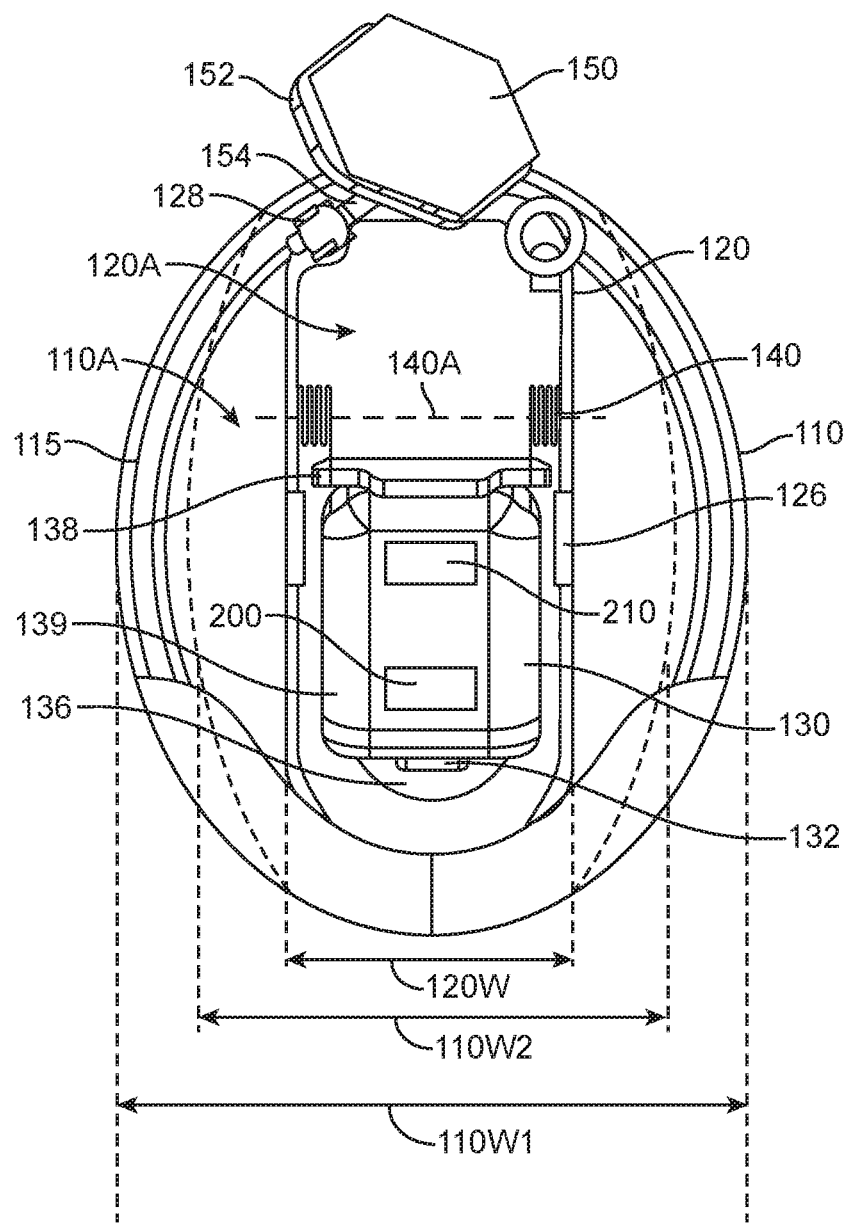
FIG. 3 shows a top view of the medial ear canal assembly of the hearing system of FIG. 1 in accordance with embodiments of the present invention.

FIG. 2 and FIG. 3 show isometric and top views, respectively, of an embodiment of medial ear canal assembly 100 according to the present invention. In the illustrated embodiments, medial ear canal assembly 100 may comprise a retention structure 110, a support structure 120, a transducer 130, at least one spring 140, and a photodetector 150. Medial ear canal assembly 100 may include data processor 200 and transmitter 210 which may be positioned on transducer 130. Retention structure 110, which may be a resilient retention structure, may be sized to couple to the tympanic membrane annulus TMA and at least a portion of the anterior sulcus AS of the ear canal EC. Retention structure 110 may comprise an aperture 110A. Aperture 110A is sized to receive transducer 130 and to allow for normal transduction of sound through the subjects hearing transduction pathway.

The retention structure 110 can be sized to the user and may comprise one or more of an O-ring, a C-ring, a molded structure, or a structure having a shape profile so as to correspond to the user's ear canal anatomy, or to a mold of the ear canal of the user. Retention structure 110 may comprise a resilient retention structure such that the retention structure can be compressed radially inward as indicated by arrows 102 from an expanded wide profile configuration to a narrow profile configuration when passing through the ear canal and subsequently expand to the wide profile configuration when placed on one or more of the eardrum, the eardrum annulus, or the skin of the ear canal. The retention structure 110 may comprise a shape profile corresponding to anatomical structures that define the ear canal. For example, the retention structure 110 may comprise a first end 112 corresponding to a shape profile of the anterior sulcus AS of the ear canal and the anterior portion of the tympanic membrane annulus TMA. The first end 112 may comprise an end portion having a convex shape profile, for example a nose, so as to fit the anterior sulcus and so as to facilitate advancement of the first end 112 into the anterior sulcus. The retention structure 110 may comprise a second end 114 having a shape profile corresponding to the posterior portion of tympanic membrane annulus TMA.

The support structure 120 may be positioned in aperture 110A and may comprise a frame, or chassis, so as to support the components connected to support structure 120. Support structure 120 may comprise a rigid material and can be coupled to the retention structure 110, the transducer 130, the at least one spring 140, which may support transducer 130, and the photodetector 150. The support structure 120 may comprise an elastomeric bumpers 122 extending between the support and the retention structure, so as to couple the support to the retention structure 110 with the elastomeric bumpers 122. The support structure 120 may define an aperture 120A formed thereon. The aperture 120A can be sized so as to receive transducer 130, which may be, for example, a balanced armature transducer. When positioned in aperture 120A, housing 139 of the balanced armature transducer 130 may extend at least partially through the aperture 120A when transducer 130 is coupled to the tympanic membrane TM. Aperture 120A may be further sized to allow normal sound conduction through medial ear canal assembly 100.

Transducer 130 may, in embodiments of the invention, comprise structures to couple to the eardrum when the retention structure 110 contacts one or more of the eardrum, the eardrum annulus, or the skin of the ear canal. The transducer 130 may, in embodiments of the invention, comprise a balanced armature transducer having a housing 139 and a vibratory reed 132 extending out one end of housing 139. Housing 139 may also, in embodiments of the invention, be a part of a flux return path for transducer 130. In embodiments of the invention, the housing may be a fully integrated part of the transducer, including, for example, the magnetic flux path. The vibratory reed 132 may be affixed to a post 134 and an umbo pad 136. The umbo pad 136 may have a convex surface that contacts the tympanic membrane TM and may move the TM in response to signals received by medial ear canal assembly 100, causing the TM to vibrate. The umbo pad 136 can be anatomically customized to the anatomy of the ear of the user.

At least one spring 140 may be connected to the support structure 120 and the transducer 130, so as to support the transducer 130 in aperture 120A. The at least one spring 140 may comprise a first spring 142 and a second spring 144, in which each spring is connected to opposing sides of a first end of transducer 130. The springs may comprise coil springs having a first end attached to support structure 120 and a second end attached to transducer 130 or a mount affixed to transducer 130, such that the coil springs pivot the transducer about axes 140A of the coils of the coil springs and resiliently urge the transducer toward the eardrum when retention structure 110 contacts one or more of the eardrum, the eardrum annulus, or the skin of the ear canal. The support structure 120 may comprise a tube sized to receiving an end of the at least one spring 140, so as to couple the at least one spring to support structure 120.

In embodiments of the invention, a photodetector 150 may be coupled to support structure 120 of medial ear canal assembly 100. A bracket mount 152 can extend substantially around photodetector 150. An arm 154 may extend between support structure 120 and bracket mount 152 so as to support photodetector 150 with an orientation relative to support structure 120 when placed in the ear canal EC. The arm 154 may comprise a ball portion so as to couple to support structure 120 with a ball-joint 128. The photodetector 150 may be electrically coupled to transducer 130 so as to drive transducer 130 with electrical energy in response to the light energy signal radiated to medial ear canal assembly 100 by input transducer assembly 20. In embodiments of the invention, medial ear canal assembly 100 may include an electronics package 215 mounted on a back surface of photodetector 150. Electronics in electronics package 215 may be used to, for example, condition or modulate the light energy signal between photodetector 150 and transducer 130. Electronics package 215 may comprise, for example, an amplifier to amplify the signal from photodetector 150.

Resilient retention structure 110 can be resiliently deformed when inserted into the ear canal EC. The retention structure 110 can be compressed radially inward along the pivot axes 140A of the coil springs such that the retention structure 110 is compressed as indicated by arrows 102 from a wide profile configuration having a first width 110W1 as illustrated in FIG. 3 to an elongate narrow profile configuration having a second width 110W2. Compression of retention structure 110 may facilitate advancement of medial ear canal assembly 12 through ear canal EC in the direction illustrate by arrow 104 in FIG. 2 and when removed from the ear canal in the direction illustrated by arrow 106 in FIG. 2. The elongate narrow profile configuration may comprise an elongate dimension extending along an elongate axis corresponding to an elongate dimension of support structure 120 (120W) and aperture 120A. The elongate narrow profile configuration may comprise a shorter dimension corresponding to a width of the support structure 120 and aperture 120A. The retention structure 110 and support structure 120 may be passed through the ear canal EC for placement on, for example, the tympanic membrane TM of a user. To facilitate placement, vibratory reed 132 of the transducer 130 can be aligned substantially with the ear canal EC while medial ear canal assembly 100 is advanced along the ear canal EC in the elongate narrow profile configuration having second width 110W2.

When properly positioned, retention structure 110 may return to a shape conforming to the ear canal adjacent to tympanic membrane TM, wherein the medial ear canal assembly is held in place, at least in part, by the interaction of retention structure 110 with the walls of ear canal EC. The medial ear canal assembly 100, including support structure 120, may apply a predetermined amount of force to the tympanic membrane TM when the umbo pad 136 is in contact with the eardrum. When medial ear canal assembly 100 is positioned the support structure 120 can maintain a substantially fixed shape and contact with the tympanic membrane TM is maintained, at least in part, by the force exerted by at least one spring 140.

Figure 4:
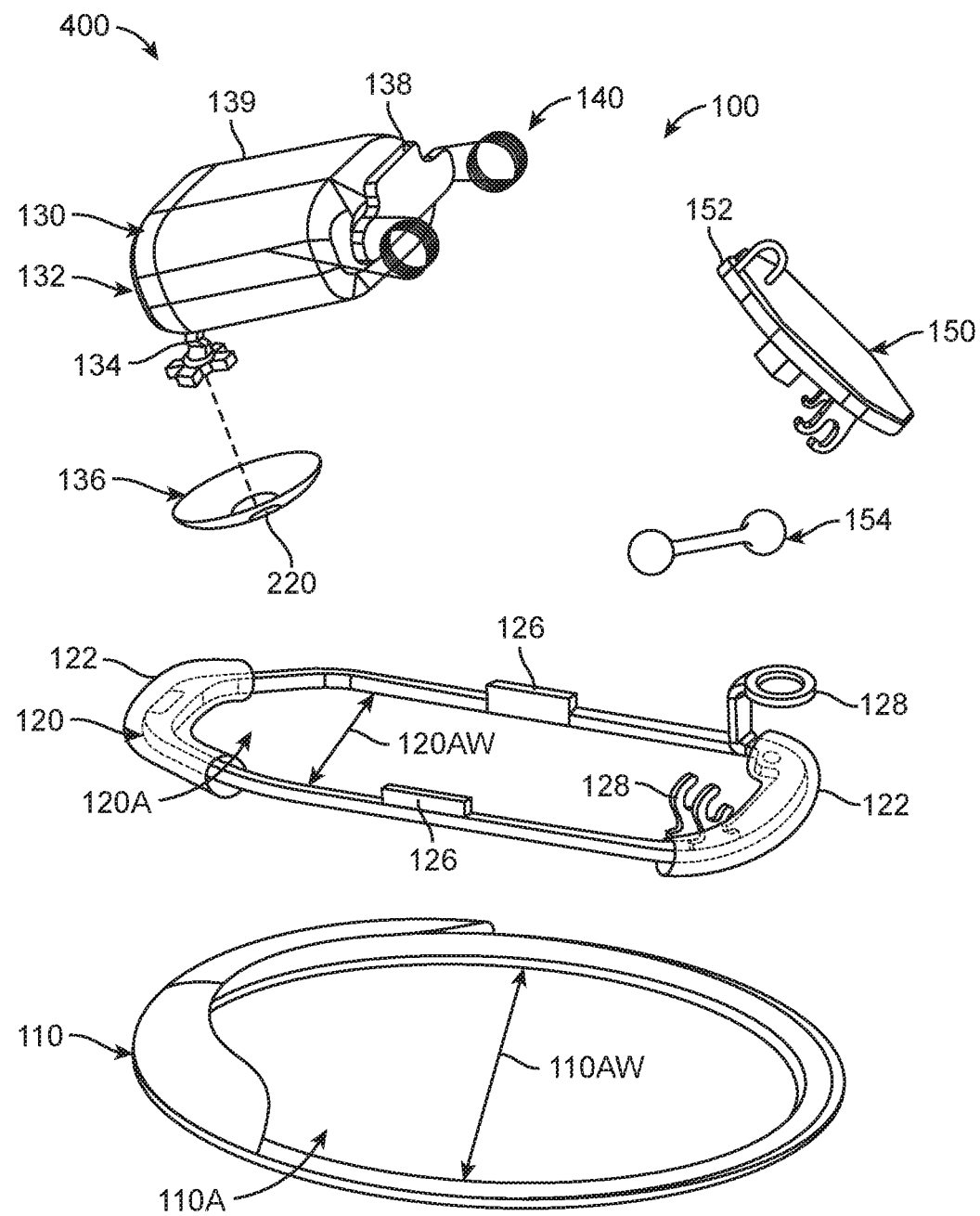
FIG. 4 shows an exploded view of a medial ear canal assembly and its method of assembly, in accordance with embodiments of the present invention.

FIG. 4 is an exploded view of a medial ear canal assembly 100 according to embodiments of the present invention which shows an assembly drawing and a method of assembling medial ear canal assembly 100. The retention structure 110 as described herein can be coupled to the support structure 120, for example, with elastomeric bumpers 122 extending between the retention structure 110 and the support structure 120. The retention structure 110 may define an aperture 110A having a width 110AW corresponding to the wide profile configuration. The support structure 120 may define an aperture 120A having a width 120AW that remains substantially fixed when the resilient retention structure is compressed. The aperture 110A of the resilient retention structure can be aligned with the aperture 120A of the support. Support structure 120 may comprise ball joint 128, and ball joint 128 can be coupled to arm 154 and bracket mount 152, such that the support is coupled to the photodetector 150.

The transducer 130 may comprise a housing 139 and a mount 138 attached to housing 139, in which the mount 138 is shaped to receive the at least one spring 140. The transducer 130 may comprise a vibratory reed 132 extending from housing 139, in which the vibratory reed 132 is attached to a post 134. The post 134 can be connected to the umbo pad 136.

The support structure 120 can be coupled to the transducer 130 with the at least one spring 140 extending between the coil and the transducer such that the umbo pad 136 is urged against the tympanic membrane TM when the medial ear canal assembly 100 is placed to transmit sound to the user. The support structure 120 may comprise mounts 126, for example tubes, and the mounts 126 can be coupled to a first end of at least one spring 140, and a second end of the at least one spring 140 can be coupled to the transducer 130 such that the at least one spring 140 extends between the support and the transducer. Umbo sensor 220 may be attached to umbo pad 136 such that umbo sensor 220 is positioned against tympanic membrane TM when medial ear canal assembly 100 is positioned in the ear canal. Umbo sensor may be positioned against any portion of the tympanic membrane and may be referred to as a tympanic membrane sensor.

Figure 5A:
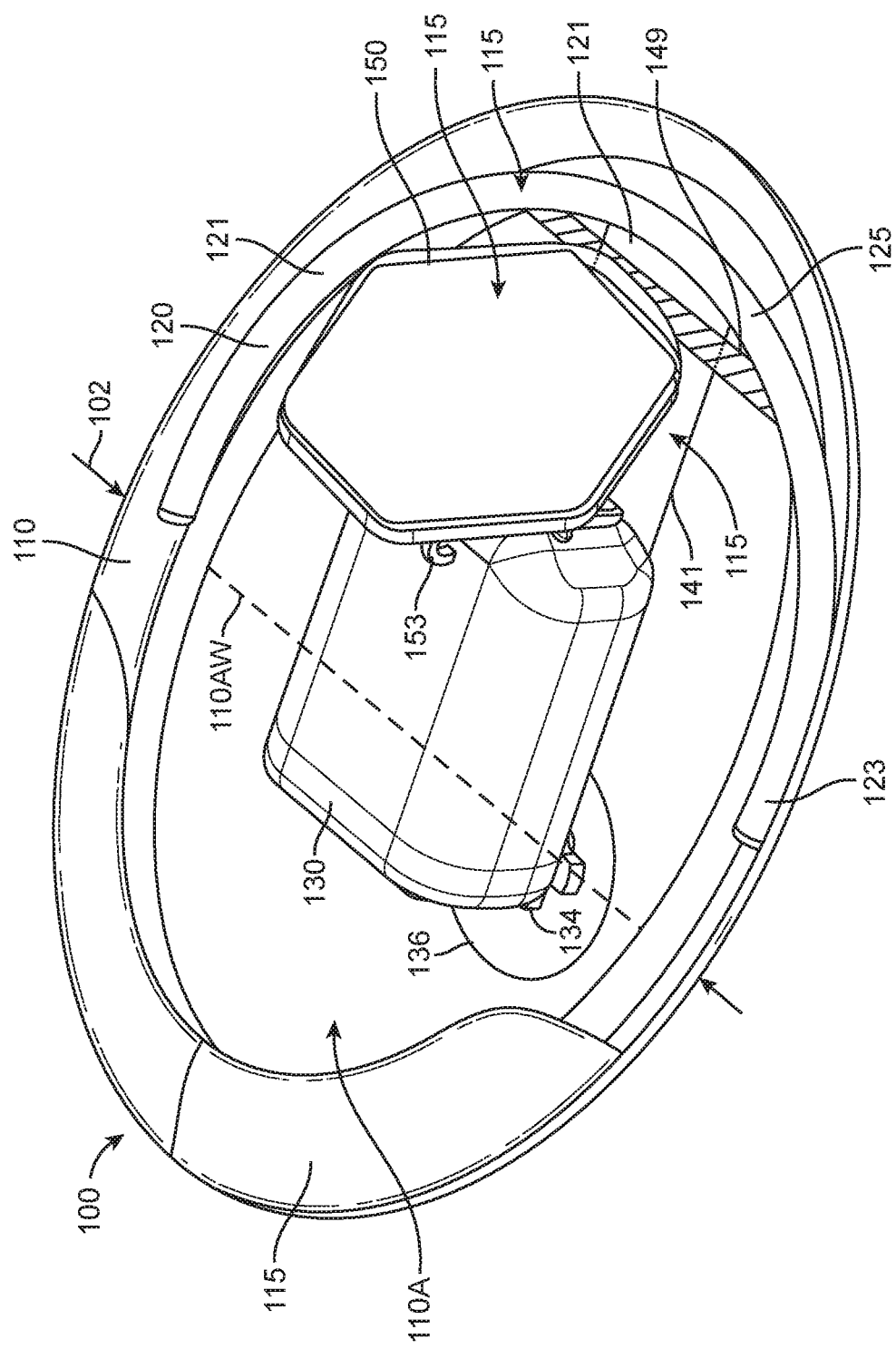
FIG. 5A is an isometric Top view of a medial ear canal assembly in accordance with embodiments of the present invention.
Figure 5B:
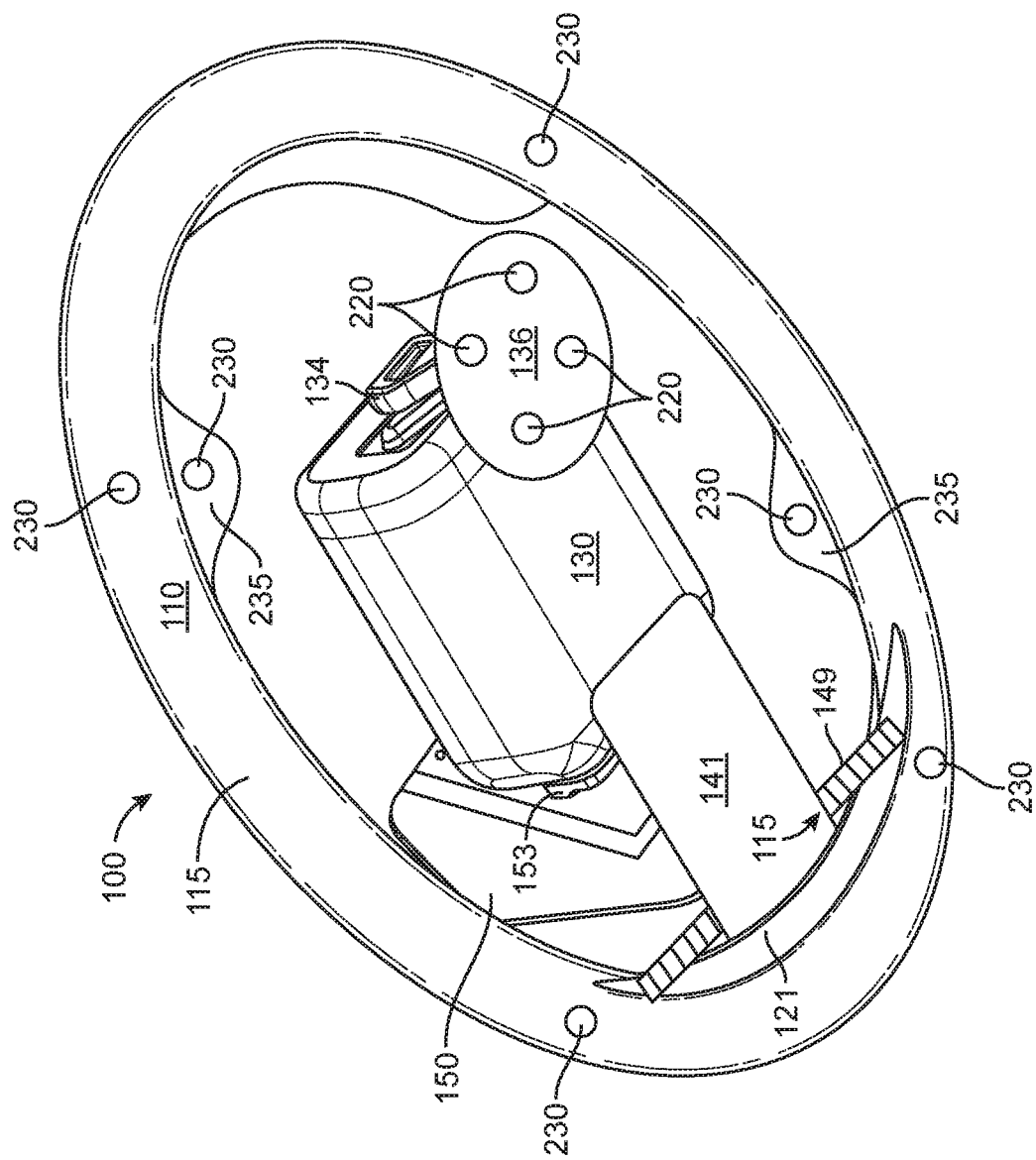
FIG. 5B is an isometric bottom view of a medial ear canal assembly in accordance with embodiments of the present invention.

FIG. 5A is an isometric top view of a medial ear canal assembly 100 according to embodiments of the invention. FIG. 5B is an isometric bottom view of a medial ear canal assembly 100 according to embodiments of the invention. In FIGS. 5A and 5B, medial ear canal assembly 100 has a retention structure 110 comprising a stiff support 121 extending along a portion of retention structure 110. The stiff support 121 may be connected to resilient member 141 and coupled to intermediate portion 149. In many embodiments, resilient member 141 and stiff support structure 120 comprise an integrated component such as an injection molded (or 3-D Printed) unitary component comprising a modulus of elasticity and dimensions so as to provide the resilient member 141 and the stiff support 121.

In the embodiments of FIGS. 5A and 5B, stiff support 121 and resilient member 141 can be configured to support output transducer 130 such that output transducer 130 is coupled to the tympanic membrane TM when the medial ear canal assembly 100, including retention structure 110 is placed in the ear canal EC. The resilient member 141 can be attached to the stiff support 121, such that the resilient member 141 directly engages the stiff support 121. The stiff support 121 can be affixed to the resilient member 141 so as to position the umbo pad 136 below the retention structure 110, such that the umbo pad 136 engages the tympanic membrane TM when the retention structure 110 is placed, for example on the tympanic membrane annulus TMA. The resilient member 141 can be configured to provide a predetermined force to the eardrum when the medial ear canal assembly 100 is placed in the Ear Canal.

In the embodiments of FIGS. 5A and 5B, resilient member 141 may comprise a resilient cantilever beam. In these embodiments, photodetector 150 may be attached to the output transducer 130 with a mount 153. Photodetector 150 and output transducer 130 can deflect together when the biasing structure 149, for example a spacer, is adjusted to couple the output transducer 130 and the umbo pad 136 to the tympanic membrane TM.

Sulcus sensors 230 may be positioned on layer 115 of retention structure 110 such that sulcus sensors 230 are in contact with the tympanic membrane TM and/or other portions of the ear canal EC when medial ear canal assembly 100 is positioned in the ear canal. Sulcus sensors 230 may also be positioned on sulcus flanges 235 to optimize their position in ear canal EC, such as, for example, to optimize their position against the tissue of tympanic membrane TM and/or against the tissue of the tympanic membrane annulus TMA. Sulcus flanges 235 may be used to, for example, position sulcus sensors 230 over regions of highly vascular tissue in the ear canal EC, such as on the tympanic membrane TM. Sulcus flanges 235 may be used to, for example, position sulcus sensors 230 over the pars tensa.

Figure 6:
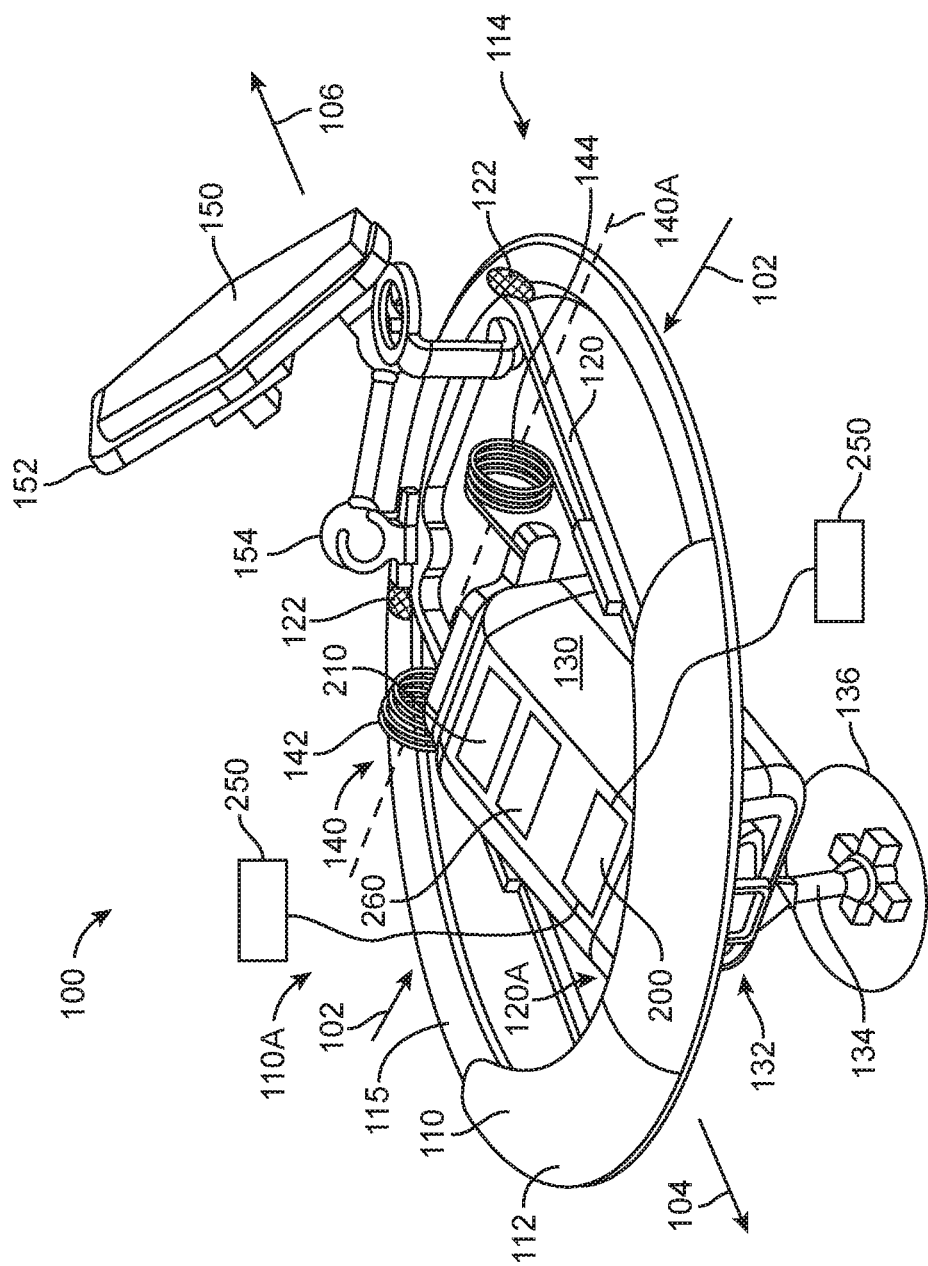
FIG. 6 shows a medial ear canal assembly in accordance with embodiments of the present invention.

FIG. 6 shows an isometric view of the medial ear canal assembly 100. Medial ear canal assembly 100 comprises a retention structure 110, a support structure 120, a transducer 130, at least one spring 140 and a photodetector 150. Medial ear canal assembly 100 may include data processor 200 and transmitter 210 which may be positioned on transducer 130. Medial ear canal assembly 100 may further include non-contact sensors 260 and tethered sensors 250. Non-contact sensors 260 and tethered sensors 250 may be connected to data processor 200 to provide data to data processor 200. Alternatively, or in combination, one or more of data processor 200, transmitter 210, non-contact sensor(s) 260 and tethered sensors 250 may be part of, located on, or connected to electronics package 215 on photodetector 150. Tethered sensors 250 may be positioned against the skin SK in the ear canal EC where umbo sensors 220 (not shown in FIG. 6) and sulcus sensors 230 (not shown in FIG. 6) cannot contact. Alternatively or in combination, one or more of non-contact sensors 260 may be positioned loosely in ear canal EC to gather data. Retention structure 110 is sized to couple to the tympanic membrane annulus TMA and at least a portion of the anterior sulcus AS of the ear canal EC. With respect to the remaining elements of the retention structure and their function, see the discussion of FIGS. 2 and 3.

Figure 7:
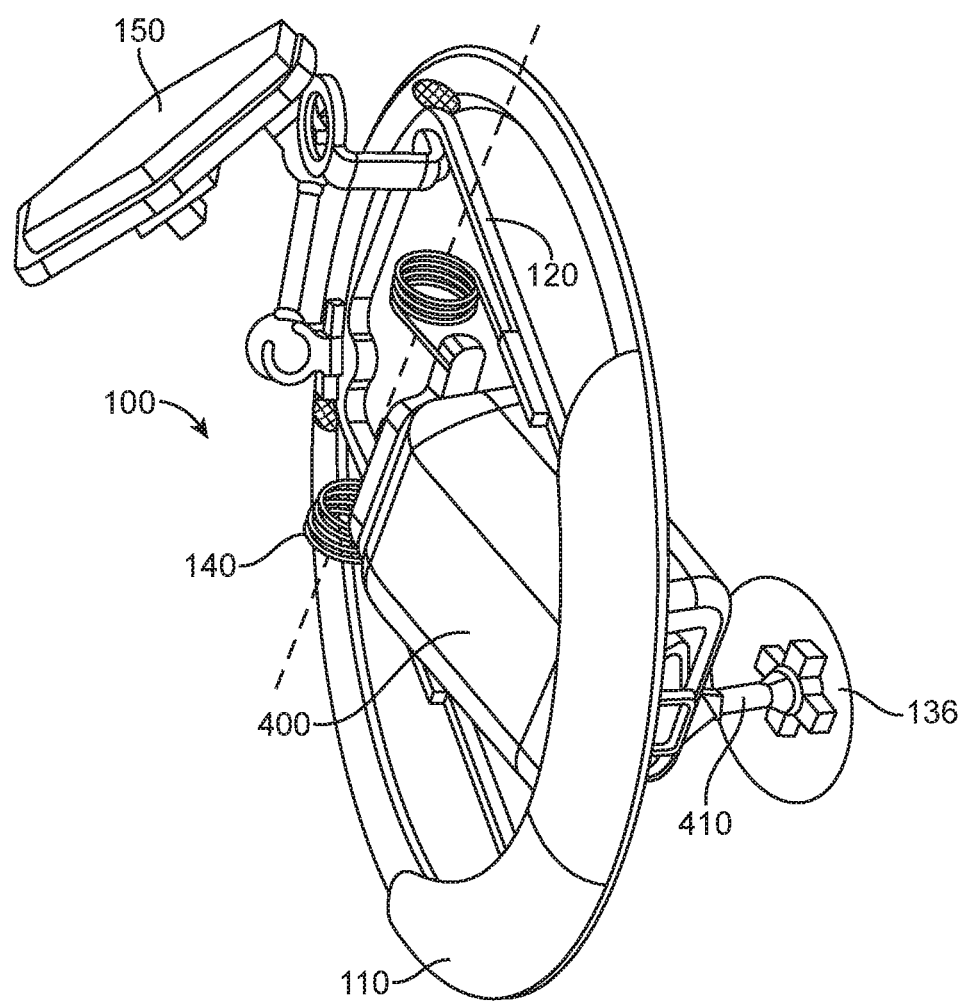
FIG. 7 shows an isometric view of a medial ear canal assembly including a drug delivery reservoir in accordance with embodiments of the present invention.

FIG. 7 shows and isometric view of the medial ear canal assembly 100 including retention structure 110, support structure 120, springs 140, a photodetector 150, and at least one drug delivery device. In embodiments of the invention, medial ear canal assembly 100 may include reservoir 400 and delivery tube 410 which are adapted to deliver drugs to the wearer. In embodiments of the invention, reservoir 400 may be used to store drugs for delivery to, for example, the tympanic membrane. In embodiments of the invention, delivery tube 410 may be used to transport drugs from reservoir 400 to umbo pad 136 which may be constructed to transmit the drugs to or through at least a portion of the tympanic membrane TM. In embodiments of the invention, umbo pad 136 may be constructed to include, for example, needles or microneedles through which drugs may be transported into the tissue of, for example, the tympanic membrane.

In embodiments of the invention, the medial ear canal assembly 100 may include sensors, such as, for example, umbo sensors 220, sulcus sensors 230 and tethered sensors 250, such as those shown in FIGS. 4, 5, and 6. In embodiments of the invention, sensors located on medial ear canal assembly 100 may be used to collect data on the user, which user data may be used to regulate the flow of drugs from the at least one drug delivery device which is incorporated into medial ear canal assembly 100.

Figure 8:
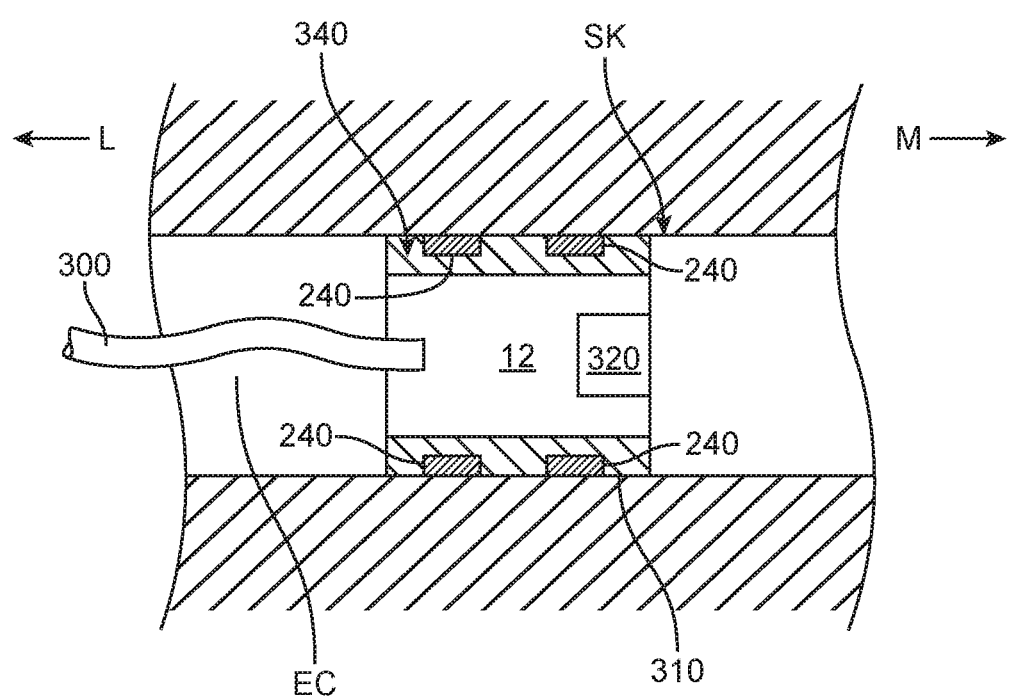
FIG. 8 shows an isometric view of a lateral ear canal assembly in accordance with embodiments of the present invention.

FIG. 8 shows a lateral ear canal assembly 12, including a retention structure 310 (which may also be referred to as an eartip retention structure) configured for placement in the ear canal. Retention structure 310 may comprise a molded tubular structure having the shape of the ear canal. Retention structure 310 may be configured to retain lateral ear canal assembly 12 in the ear canal. Lateral ear canal assembly 12 may include a signal source 320 such as a laser diode. An outer surface 340 of retention structure 310 may include ear tip sensors 240, which may be positioned against the skin SK of the ear canal EC and, alternatively or in combination, sensors (not shown) which are positioned on the medial or lateral ends of lateral ear canal assembly 12, such as, for example, a body temperature sensor.

Figure 9:
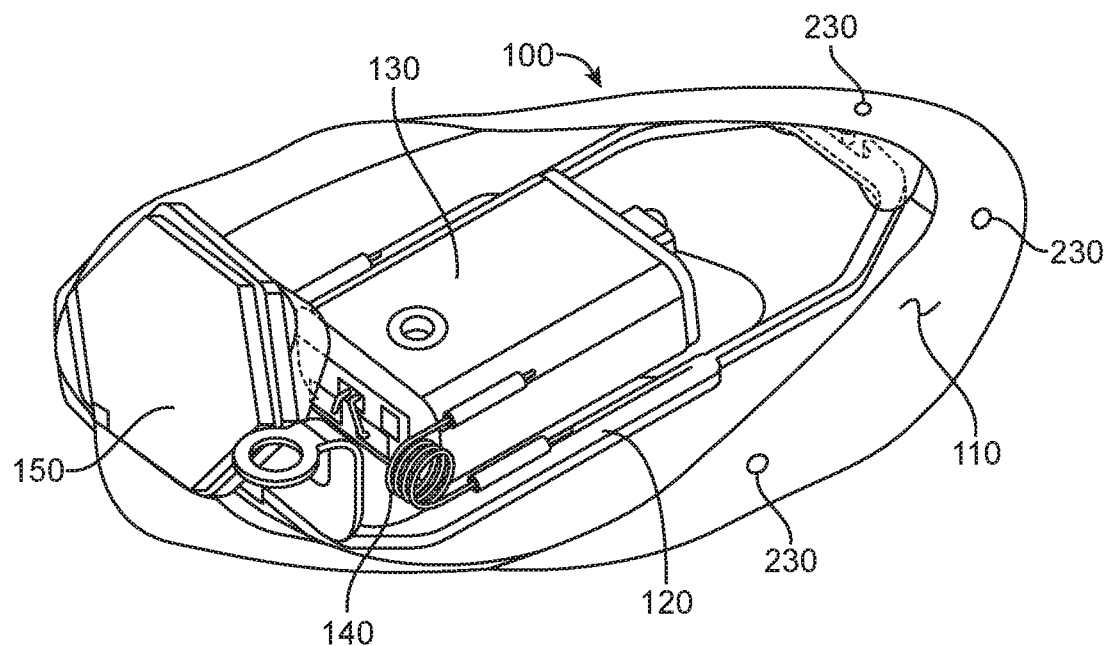
FIG. 9 is an isometric top view of a medial ear canal assembly in accordance with embodiments of the present invention.

FIG. 9 is an isometric Top view of a medial ear canal assembly in accordance with embodiments of the present invention. In FIG. 9, medial ear canal assembly 100 comprises transducer 130, photodetector 150, spring 140, support structure 120 and retention structure 110. In the embodiment of FIG. 9, sulcus sensors 230 may be positioned on retention structure 110, which may be, for example a flexible material adapted to conform to the anatomy of the user's ear canal. Retention structure 110 may comprise a material such as Parylene or Silicone.

Figure 10:
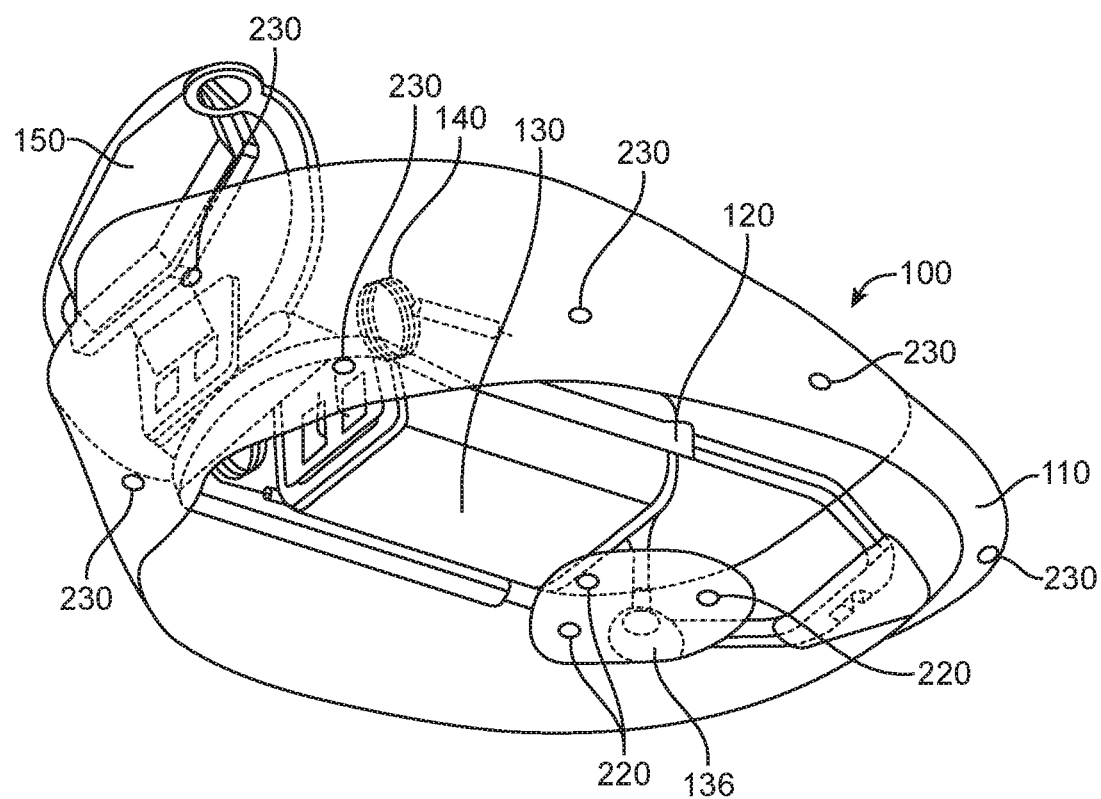
FIG. 10 is an isometric bottom view of a medial ear canal assembly in accordance with embodiments of the present invention.

FIG. 10 is an isometric bottom view of a medial ear canal assembly in accordance with embodiments of the present invention. In FIG. 10, medial ear canal assembly 100 may comprise transducer 130, photodetector 150, spring 140, support structure 120, retention structure 110 and umbo pad 136. In the embodiment of FIG. 10, sulcus sensors 230 may be positioned on retention structure 110, which may be, for example a flexible material adapted to conform to the anatomy of the user's ear canal. In the embodiment of FIG. 10, umbo sensors 220 may be positioned on umbo pad 136. Retention structure 110 may comprise a material such as Parylene or Silicone.

In embodiments of the invention, umbo sensors 220, sulcus sensors 230, eartip sensors 240, and tethered sensors 250 may comprise sensors that contact the skin to detect biometric data. Alternatively or in combination, umbo sensors 220, sulcus sensors 230, eartip sensors 240, and tethered sensors 250 may comprise sensors that do not require skin contact to detect biometric data. Non-contact sensors may also be sensors which do not require skin contact to detect biometric data.

Skin contacting sensors adaptable for use in embodiments of the present invention may include: micro-sensors, electrochemical sensors; thin film sensors; pressure sensors; micro-needle sensors, capacitive sensors thermometers, thermocouples, trigeminal nerve monitors; piezoelectric sensors; electrodes, pulse oximetry sensors, glucose meters, oxygen sensors and iontophoresis electrodes.

Non-skin contacting sensors adaptable for use in embodiments of the present invention may include: light sensors (e.g. optical sensors or infrared sensors); sound sensors (e.g. a microphone to pick up sounds in the ear canal); vibration sensors; heat sensors, micro-sensors; electrochemical sensors; thin film sensors; liquid (e.g. oil) sensors; accelerometers, microphones; gyroscopes, including 3-axis accelerometers, 3 axis gyroscopes; MEMS sensors, including 3 axis MEMS sensors; GPS circuitry; pedometers; reservoir monitors; walking gait sensors; battery state monitors; energy level monitors; and strain gauges.

In embodiments of the present invention, a suitable microphone might be transducer 130 wired to measure back electromagnetic fields (back EMF) which is generated when post 134 is moved independent of any drive signal provided to transducer 130, such as by vibrations in the tympanic membrane TM resulting from, for example the user speaking or snoring. The back EMF could then be provided to data processor 200 where it could be analyzed and transmitted to a receiver in lateral ear canal assembly 12 or in a remote receiver (e.g. a smart phone) by transmitter 210. In one embodiment of the invention, data processor 200 could include circuitry used to separate sounds coming from sources other than the user from sounds generated by the user to provide filtered data, which filtered feedback data may represent, for example, the user's voice.

In embodiments of the invention, a suitable optical sensor may comprise an infrared transmitter and infrared receiver. In embodiments of the invention, a suitable optical sensor may include an optical receiver tuned to the same frequency as signal source 320.

In embodiments of the invention, sensors may be 3D printed on or as an integral part of structures in the components of hearing system 10. In embodiments of the invention, non-skin contacting sensors may be mounted on, for example, the back side of photodetector 150.

In embodiments of the invention, a light may be mounted on medial ear canal assembly 100 and positioned to shine through tympanic membrane TM to illuminate the middle ear and the contents thereof. In embodiments of the invention, a sensor may be further included on medial ear canal assembly 100 to measure light reflected from the middle ear.

In embodiments of the invention, sensors on medial ear canal assembly 100 may be used to sense the position of transducer assembly with respect to structural features of the ear canal EC, such as the tympanic membrane TM. The data from such sensors may be used to position the medial ear canal assembly 100 to ensure it is properly placed and aligned in the user's ear.

In embodiments of the invention, sensors on medial ear canal assembly 100 or positioned in the ear canal EC may be used to measure environmental factors which are related to the proper functioning of the medial ear canal assembly 100, such as, degradation in photodetector output, earwax buildup, whether the user is compliant with the required oiling regimine. In embodiments of the invention, sensors may be used to ensure that the user is properly oiling by, for example, measuring the amount and regularity of oiling. In embodiments of the invention, sensors on the eartip may be used to guide and/or detect proper medial ear canal assembly insertion. In embodiments of the invention, pressure sensors and/or fluid sensors may be positioned on a medial ear canal assembly, including on the umbo pad 136 or sulcus platform to assist in the preceding tasks.

In embodiments of the invention, strain gauges may be included in the medial ear canal assembly 100 to provide feedback on the proper placement of medial ear canal assembly 100. For example, post 134 may include strain gauges which indicate when displacement starts and/or the degree of displacement by registering the lateral force on umbo pad 136. Further, the placement of one or more strain gages on retention structure 110 may provide an indication that the medial ear canal assembly 100 has lifted off of the tympanic membrane TM. In embodiments of the invention, medial ear canal assembly 100 may include features which interact with physical features of the wearer to maintain medial ear canal assembly 100 in a predetermined position in the ear canal EC, such as, for example against the tympanic membrane TM. In embodiments of the invention, such physical features may create strain on the medial ear canal assembly 100, which strain may be measured by strain gauges positioned on medial ear canal assembly 100 to ensure proper placement of medial ear canal assembly 100.

In embodiments of the invention, a feedback signal representative of the average power received by photodetector 150 may be provided, which signal may be used to quantify the coupling efficiency between photodetector 150 and signal source 320. In embodiments of the invention, the power level of signal source 320 may be adjusted to reflect the degree of coupling and the coupling efficiency indicated by the feedback signal. In embodiments of the invention, the position of lateral ear canal assembly 12 and/or medial ear canal assembly 100 may be modified to increase or decrease the level of the feedback signal, thus improving the coupling efficiency between the lateral ear canal assembly 12 and the medial ear canal assembly 100.

In embodiments of the invention, noise cancelation may be implemented by, for example, incorporating a microphone onto the back of photodetector 150. Sound signals received by the microphone could be converted into drive signals which move the tympanic membrane in opposition to the received signals such that the received signals are not perceived by the user. Such noise cancelation may be implemented such that the microphone is turned on only when the output from the photodetector exceeds a predetermined voltage, such as, for example, approximately 300 millivolts. Alternatively or in combination, the microphone may be turned on when the photodetector output voltage exceeds approximately 1 volt. In one embodiment of the invention, the sound signals may be measured by measuring the back EMF of transducer 130 and generating a signal to the transducer which causes the transducer to vibrate the tympanic membrane in a way which cancels the movement which generated the measured back EMF.

In embodiments of the present invention, sensors on medial ear canal assembly 100 or positioned in the ear canal EC may be used to measure bodily fluids, such as sweat, interstitial fluid, blood and/or cerumen (ear wax). Sensors suitable for making these measurements include electrochemical sensors, micro-needles and capacitive sensors.

In embodiments of the present invention, sensors on medial ear canal assembly 100 or positioned in the ear canal EC may be used to measure sweat for the purpose of, for example, measuring hydration levels, electrolyte balance, lactate threshold, glucose levels, calories burned, respiration rate, drug levels, metabolites, small molecules (e.g. amino acids, DHEA, cortisol, pH levels and various proteins. Sensors suitable for making these measurements include electrochemical sensors, micro-needles and capacitive sensors.

In embodiments of the present invention, sensors on medial ear canal assembly 100 or positioned in the ear canal EC may be used to measure the temperature, including the core body temperature of a user. Sensors suitable for making these measurements include thermometers, thermocouples, and optical temperature sensors.

In embodiments of the present invention, sensors on medial ear canal assembly 100 or positioned in the ear canal EC may be used to measure and/or monitor blood pressure, blood flow, heart rate, pulse, and arrhythmia. Sensors suitable for making these measurements include electrodes, PPG (Photoplethysmography) sensors and pulse oximetry sensors.

In embodiments of the present invention, sensors on medial ear canal assembly 100 or positioned in the ear canal EC may be used to measure and/or monitor the oxygen level in a user's blood. Sensors suitable for making these measurements include optical sensors PPG (Photoplethysmography) sensors, and/or pulse oximetry sensors.

In embodiments of the present invention, sensors on medial ear canal assembly 100 or positioned in the ear canal EC may be used to measure and/or monitor drug delivery and/or medication use by monitoring the drug content in blood or interstitial fluid of a user. Sensors suitable for making these measurements include micro-needles and/or iontophoresis electrodes.

In embodiments of the present invention, sensors on medial ear canal assembly 100 or positioned in the ear canal EC may be used to measure and/or monitor body fat. Sensors suitable for making these measurements include electrodes.

In embodiments of the present invention, sensors on medial ear canal assembly 100 or positioned in the ear canal EC may be used to monitor and/or measure sleep, including the duration and/or quality of such sleep. Sensors suitable for making these measurements include accelerometers, microphones and gyroscopes.

In embodiments of the present invention, sensors on medial ear canal assembly 100 or positioned in the ear canal EC may be used to measure and/or monitor snoring and/or sleep apnea. Sensors suitable for making these measurements include accelerometers, microphones; gyroscopes; head position monitors (3 axis gyroscope); vibration sensor (microphone, TMT microactuator); oxygen sensors and trigeminal nerve monitors.

In embodiments of the present invention, sensors on medial ear canal assembly 100 or positioned in the ear canal EC and/or on the tympanic membrane may be used to measure and/or monitor the location of a user. Sensors suitable for making these measurements include GPS circuitry.

In embodiments of the present invention, sensors on medial ear canal assembly 100 or positioned in the ear canal EC may be used to measure and/or monitor the movement of a user. Sensors suitable for making these measurements include an accelerometer and/or a pedometer.

In embodiments of the present invention, sensors on medial ear canal assembly 100 or positioned in the ear canal EC may be used to measure and/or monitor calorie intake. Sensors suitable for making these measurements include microphones and piezoelectric sensors.

In embodiments of the present invention, sensors on medial ear canal assembly 100 or positioned in the ear canal EC may be used to measure and/or monitor posture, head position and/or body position. Sensors suitable for making these measurements include gyroscopes, accelerometers (including 3-axis accelerometers) and MEMS sensors (including 3 axis MEMS sensors).

In embodiments of the present invention, sensors on medial ear canal assembly 100 or positioned in the ear canal EC may be used to measure and/or monitor seizure disorders, including epilepsy, by making electroencephalogram (EEG) measurements. Sensors suitable for making these measurements include electrodes and/or electroencephalograph.

In embodiments of the present invention, sensors on medial ear canal assembly 100 or positioned in the ear canal EC may be used to measure and/or monitor electrical activities of the heart by making an electrocardiogram (ECG/EKG). Sensors suitable for making these measurements may include electrodes and/or electrocardiographs.

In embodiments of the present invention, sensors on medial ear canal assembly 100 or positioned in the ear canal EC may be used to measure and/or monitor the electrical activity produced by skeletal muscles by making an electromyogram using Electromyography (EMG). Sensors suitable for making these measurements may include electrodes and/or electromyographs.

In embodiments of the present invention, sensors on medial ear canal assembly 100 or positioned in the ear canal EC may be used to measure and/or monitor the glucose in a user's blood and/or interstitial fluid. Sensors suitable for making these measurements include glucose meters, electrochemical sensors, microneedles, and/or iontophoresis electrodes.

In embodiments of the present invention, sensors on medial ear canal assembly 100 or positioned in the ear canal EC may be used to measure and/or monitor neurological function. Sensors suitable for making these measurements may include sensors for measuring the walking gait of a user.

In embodiments of the present invention, sensors on medial ear canal assembly 100 or positioned in the ear canal EC may be used to measure and/or monitor the position and/or orientation of a user's eye.

Many other physical characteristics may be measured by sensors on medial ear canal assembly 100 or positioned in the ear canal EC, including: multi-axis acceleration; multi-axis angle; skin capacitance; infrared absorption, (e.g. pulse ox), chemical reactions; and strains.

In embodiments of the present invention, devices on medial ear canal assembly 100 or positioned in the ear canal EC may be used in combination with sensors to deliver medication to a user. Devices suitable for making these delivers may include drug reservoirs, patches, microneedles, polymers designed to elute over time and/or drug eluting materials.

In embodiments of the invention, drugs may be delivered through, for example, iontophoresis, direct skin contact, needles, drugs in the platform, drug infused silicon or other structural materials or holes or pores in the tympanic membrane structure to hold drugs prior to dispensing or weep over time.

In embodiments of the present invention, devices on medial ear canal assembly 100 or positioned in the ear canal EC may be used to stimulate serotonin production in a user by, for example, shining light in the ear canal EC for predetermined periods of time. Alternatively, such devices may be adapted to increase the production of vitamin D.

In embodiments of the present invention, devices, including sensors on medial ear canal assembly 100 or positioned in the ear canal EC may be used to recognize the speech of a user. Devices suitable for making these delivers may include microphones and speech recognition/signal processing chips and software.

In embodiments of the present invention, sensors on medial ear canal assembly 100 or positioned in the ear canal EC may be used to control the function of hearing system 10. The function of hearing system 10 may be controlled by, for example, sensing control instructions from the user, including, verbal instructions and/or instructions conveyed by finger snapping, bone conduction and/or bringing a hand or finger into proximity with the sensors on medial ear canal assembly 100. Sensors suitable for such control functions may include touch sensors, bone conduction sensors and proximity sensors.

In embodiments of the present invention, the power required to operate sensors, drug delivery, and/or other devices located on medial ear canal assembly 100 may be supplied by one or more of the following: AC or DC current from photodetector 150; AC or DC current from an RF antenna located on or connected to medial ear canal assembly 100; Energy from a battery, micro-battery and/or super capacitor on or connected to medial ear canal assembly 100. In further embodiments of the present invention, circuitry on medial canal assembly 100 may be obtained by, for example: harvesting power from the motion of the user, including the dynamic motion of the wall of an outer ear, using, for example, a spring located on or connected to medial ear canal assembly 100; harvesting power from the motion of the tympanic membrane, including harvesting sound energy which vibrates the tympanic membrane; harvesting power from the motion of the tympanic membrane, including harvesting sound energy below approximately 100 Hz; harvesting power from the action of muscles in or near the ear canal, such as, for example muscles used in chewing food; harvesting power from the temporomandibular joint; using the movement of the eardrum (such as, for example, driven by music) to act as a pump. In embodiments of the invention circuitry on medial ear canal assembly 100 may be powered by, for example, the use of light based earplugs which transmits energy to medial ear canal assembly 100 to power the assembly when lateral ear canal assembly 12 is not being used. In embodiments of the invention, such light based earplugs may be used to recharge batteries or super capacitors located on or connected to medial ear canal assembly 100. In embodiments of the invention circuitry on medial ear canal assembly 100 may be powered by, for example, a wand which radiates, for example, RF energy to an antenna located on or connected to medial ear canal assembly 100 to power sensors on medial ear canal assembly 100 and/or in the ear canal EC for the purpose of making measurements.

In embodiments of the present invention, sensors located on medial ear canal assembly 100 may communicate data to any one of a number of devices, including lateral ear canal assembly 12, a smartphone, a smart watch, a cellular network, a ZigBee network, a Wi-Fi network, a WiGi-G network, and/or a Bluetooth enabled device. In embodiments of the present invention, such information may be transmitted from medial ear canal assembly 100 to lateral ear canal assembly 12 and from lateral ear canal assembly 12 to a smartphone, a smart watch, a cellular network, a ZigBee network, and/or a Bluetooth enabled device. In embodiments of the invention, such sensors a part of a closed loop communication network. In embodiments of the invention, communication to medial ear canal assembly 100 may be facilitated by the positioning of an antenna on or connected to medial ear canal assembly 100. In embodiments of the invention, such antennas may be printed on or formed as part of a chassis of medial ear canal assembly 100. In embodiments of the present invention, communication of data may be facilitated by the inclusion of transmitter 210 on medial ear canal assembly 100.

In embodiments of the invention, removable portions of hearing system 10 may sense emergency situations, such as fire alarms, and communicate with the user wearing medial ear canal assembly 100 using an antenna located on or connected to medial ear canal assembly 100 to warn the user of danger.

In embodiments of the invention, data collected from sensors located on medial ear canal assembly 100 or in the ear canal EC of a user may be communicated to the user's physician and/or family. In embodiments of the invention, data collected from sensors located on medial ear canal assembly 100 or in the ear canal EC of a user may be used to generate data or reports which may be communicated to the user's physician and/or family. In embodiments of the present invention, information, data or reports which may be communicated to the user, the user's physician and/or family may include information on the user's environment, including time of day, activity, surrounding sounds. In embodiments of the present invention, information, data or reports which may be communicated to the user, the user's family physician, and/or family may include information on biometric date related to the user, including blood pressure, heart rate, glucose levels, and other biometric data. In embodiments of the present invention, information, data or reports which may be communicated to the user, the user's family physician and/or family may include information on specific events related to the user or the user's physical condition, including, falls, blood pressure spikes, heart attacks, temperature spikes, impending or actual seizures, changes in specific biomarkers, or other metrics. In embodiments of the present invention, information, data or reports which may be communicated to the user, the user's family physician and/or family may include algorithm results transmitted when trends or parameters in the user's biometric data become concerning. In embodiments of the present invention, information, including warnings may be communicated to the user may include, sleep apnea warnings, drowsiness warnings (e.g. when driving), warnings of impending seizures, migraine headaches warnings, and/or cluster headache warnings.

In embodiments of the invention, medial ear canal assembly 100 may be used to communicate with the user to, for example, remind the user when to drink or when the user's sugar levels are spiking or dropping.

In embodiments of the present invention, data or other information may be transmitted by a user to the hearing system 10 of a second user. In embodiments of the invention, a user may transmit data or other information to a network of hearing systems 10.

In embodiments of the present invention, data collected by sensors positioned on medial ear canal assembly 100 or in the ear canal of a user may be collected and analyzed, by, for example, an Application on the user's smart phone. Such data may be used for many purposes, including predicating changes in the user's health and generating event alarms. Event alarms generated from the collected data might include alarms related to epilepsy seizures, migraines, cluster headaches, or predetermined changes in key biometric data or trends. Such data may be further processed to allow the user to, for example, view the data which is most important to the user, perform trend analysis on the data, correlate specific data with activities or environment, provide a dashboard of data or chart specific data. Data may also be stored for review at future doctor's appointments. Data trends may also be stored and analyzed over time.

Embodiments of the present invention are directed to a hearing system comprising a medial ear canal assembly including a transducer configured to be positioned on the tympanic membrane of a user; a lateral ear canal assembly including a signal source configured to be positioned in the ear canal of a user; and sensors connected to the medial ear canal assembly, the sensors being connected to a transmitter. In embodiments of the invention, the sensors may include sensors adapted to detect biometric data. In embodiments of the invention, the sensors may include sensors adapted to detect one or more physical characteristics of the user. In embodiments of the invention, at least one of the sensors may comprise a microphone. In embodiments of the invention, the microphone may comprise a micro-actuator. In embodiments of the invention, sound received by the micro-actuator is configured to be converted to a back EMF signal. In embodiments of the invention, the hearing system may include a data processor which is configured to convert the back EMF to a signal representative of the sound received by the micro-actuator. In embodiments of the invention the hearing system may be configured to transmit the signal representative of the sound received by the microactuator to a receiver external to the hearing system. In embodiments of the invention, the receiver comprises a smart phone, a wireless network, or a peripheral device. In embodiments of the invention, at least one of the sensors comprises a skin contacting sensor or a non-skin contacting sensor. In embodiments of the invention, at least one of the sensors comprises an umbo sensor, an eartip sensor, or a tethered sensor.

Embodiments of the present invention are directed to a method of sensing physical characteristics of a hearing system user, the hearing system comprising a medial ear canal assembly positioned on or near the tympanic membrane, the medial ear canal assembly comprising transducer sensors and a transmitter, the method comprising the steps of: using the sensors to measure biometric data of the user; and transmitting the measured biometric data using the transmitter. In embodiments of the invention the method further comprising using the sensors to measure one or more physical characteristics of the user. In embodiments of the invention at least one of the sensors comprises a microphone the method further comprising the steps of measuring sound in the user's ear canal. In embodiments of the invention the microphone comprises a micro-actuator, the method further comprising measuring the back EMF signal. In embodiments of the invention the hearing system includes a data processor, the method further including the step of converting the back EMF signal to an electrical signal and transmitting the electrical signal to the data signal processor. In embodiments of the invention the back EMF signal includes a first signal portion representative of the signal received from the hearing system and a second signal representative of at least one physical characteristic of the user, the method further including the step of separating the first signal from the second signal. In embodiments of the invention the method further includes the step of transmitting the signal to a receiver external to the hearing system. In embodiments of the invention the receiver comprises a smart phone. In embodiments of the invention at least one of the sensors comprises a skin contacting sensor or a non-skin contacting sensor. In embodiments of the invention at least one of the sensors comprises an umbo sensor, an eartip sensor, or a tethered sensor. In embodiments of the invention the output transducer is used as a sensor. In embodiments of the invention the sensor is used as a microphone to measure received sound at the tympanic membrane. In embodiments of the invention the signal from the microphone is coupled to the transmitter.

Embodiments of the present invention are directed to an ear canal platform comprising: a medial ear canal assembly positioned on or over the tympanic membrane of a user; and sensors connected to the signal output transducer, the sensors being connected to a transmitter. In embodiments of the invention the sensors include sensors adapted to detect biometric data. In embodiments of the invention the sensors include sensors adapted to detect one or more physical characteristics of the user. In embodiments of the invention at least one of the sensors comprises a microphone. In embodiments of the invention the microphone comprises a micro-actuator. In embodiments of the invention sound received by the micro-actuator is configured to be converted to a voltage representative of the back EMF generated in the microactuator by the sound received by the microactuator. In embodiments of the invention the hearing system includes a data processor which is configured to convert the voltage to a signal representative of the sound received by the micro-actuator. In embodiments of the invention the signal is configured to be transmitted by the hearing system to a receiver external to the hearing system. In embodiments of the invention the receiver comprises a smart phone, a wireless network, or a peripheral device. In embodiments of the invention at least one of the sensors comprises a skin contacting sensor or a non-skin contacting sensor. In embodiments of the invention at least one of the sensors comprises an umbo sensor, an eartip sensor, or a tethered sensor.

Embodiments of the present invention are directed to a method of sensing physical characteristics of a user having a medial ear canal assembly positioned on or near the tympanic membrane, the medial ear canal assembly comprising sensors and a transmitter, the method comprising the steps of: using the sensors to measure biometric data of the user; and transmitting the measured biometric data using the transmitter. In embodiments of the invention the method further comprising using the sensors to measure one or more physical characteristics of the user. In embodiments of the invention at least one of the sensors comprises a microphone the method further comprising the steps of measuring sound in the user's ear canal. In embodiments of the invention the microphone comprises a micro-actuator, the method further comprising measuring and transmitting the output of the microphone. In embodiments of the invention the hearing system includes a data processor, the method further including the step of sending the transmitted signal to the data processor. the transmitted signal includes a first signal portion representative of the signal received from the hearing system and a second signal representative of a physical characteristic of the user, the method further including the step of separating the first signal from the second signal. In embodiments of the invention the method further includes the step of transmitting the signal to a receiver external to the hearing system. In embodiments of the invention the receiver comprises a smart phone. In embodiments of the invention at least one of the sensors comprises a skin contacting sensor or a non-skin contacting sensor. In embodiments of the invention at least one of the sensors comprises an umbo sensor, an eartip sensor, or a tethered sensor. In embodiments of the invention the output transducer is used as a sensor. In embodiments of the invention the sensor is used as a microphone to measure received sound at the tympanic membrane. In embodiments of the invention the signal from the microphone is coupled to the transmitter.

Embodiments of the present invention are directed to an ear canal platform comprising: a medial ear canal assembly positioned on the tympanic membrane of a user; a drug delivery device mounted on the ear canal assembly. In embodiments of the invention an ear canal assembly further includes sensors connected to the ear canal assembly, the sensors being connected to a transmitter. In embodiments of the invention the sensors include sensors adapted to detect biometric data. In embodiments of the invention the sensors include sensors adapted to detect one or more physical characteristics of the user. In embodiments of the invention at least one of the sensors is a microphone. In embodiments of the invention the microphone is a micro-actuator. In embodiments of the invention sound received by the micro-actuator is converted to a transmitted signal. In embodiments of the invention the hearing system includes a data processor which converts the transmitted signal to a signal representative of the sound received by the micro-actuator. In embodiments of the invention the signal is transmitted by the hearing system to a receiver external to the hearing system. In embodiments of the invention the receiver is a smart phone, a wireless network, or a peripheral device. In embodiments of the invention at least one of the sensors comprises a skin contacting sensor, or a non-skin contacting sensor. In embodiments of the invention at least one of the sensors comprises an umbo sensor, an eartip sensor, or a tethered sensor.

Embodiments of the present invention are directed to a method of delivering drugs to a user having a medial ear canal assembly positioned on or near the user's tympanic membrane, the medial ear canal assembly comprising a drug delivery device, the method comprising the steps of: delivering drugs to the user through the drug delivery device. In embodiments of the invention the medial ear canal assembly further includes sensors and a transmitter, the method comprising the steps of: using the sensors to measure biometric data of the user; and transmitting the measured biometric data using the transmitter. In embodiments of the invention the method further includes the step of activating the drug delivery device using the biometric data measured by the sensors. In embodiments of the invention the method further comprises using the sensors to measure one or more physical characteristics of the user. In embodiments of the invention the method further comprises the step of activating the drug delivery device using the measured physical characteristics of the user. In embodiments of the invention, the step of activating drug delivery includes activating drug delivery when needed and/or at predetermined times or over predetermined time periods. In embodiments of the invention at least one of the sensors comprises a skin contacting sensor or a non-skin contacting sensor. In embodiments of the invention at least one of the sensors comprises an umbo sensor, an eartip sensor, or a tethered sensor. In embodiments of the invention, the system may comprise a reservoir and mechanisms for drug delivery.

While the preferred embodiments of the devices and methods have been described in reference to the environment in which they were developed, they are merely illustrative of the principles of the present inventive concepts.

Modification or combinations of the above-described assemblies, other embodiments, configurations, and methods for carrying out the invention, and variations of aspects of the invention that are obvious to those of skill in the art are intended to be within the scope of the claims. In addition, where this application has listed the steps of a method or procedure in a specific order, it may be possible, or even expedient in certain circumstances, to change the order in which some steps are performed, and it is intended that the particular steps of the method or procedure claim set forth herein below not be construed as being order-specific unless such order specificity is expressly stated in the claim.

The invention claimed is:

1. A system comprising:
    a medial ear canal assembly including a transducer configured to be positioned on a tympanic membrane of a user;
    a lateral ear canal assembly including a signal source configured to be positioned in an ear canal of a user; and
    sensors connected to the medial ear canal assembly, the sensors being connected to a transmitter, wherein the sensors include sensors adapted to detect biometric data.

2. A system according to claim 1, wherein the sensors include sensors adapted to detect one or more physical characteristics of the user.

3. A system according to claim 1, wherein at least one of the sensors comprises a microphone.

4. A system according to claim 3, wherein the microphone comprises a micro-actuator.

5. A system according to claim 4, wherein sound received by the micro-actuator is configured to be converted to a back EMF signal.

6. A system according to claim 5, wherein the system includes a data processor which is configured to convert the back EMF signal to a signal representative of the sound received by the micro-actuator.

7. A system according to claim 6, wherein the system is configured to transmit the signal representative of the sound received by the micro-actuator to a receiver external to the system.

8. A system according to claim 7, wherein the receiver comprises a smart phone, a wireless network, or a peripheral device.

9. A system according to claim 1, wherein at least one of the sensors comprises a skin contacting sensor or a non-skin contacting sensor.

10. A system according to claim 1, wherein at least one of the sensors comprises an umbo sensor, an eartip sensor, or a tethered sensor.

11. A method of sensing physical characteristics of a system user, the system comprising a medial ear canal assembly configured to be positioned on or near a tympanic membrane of the system user, the medial ear canal assembly comprising transducer sensors and a transmitter, the method comprising the steps of:
    using the sensors to measure biometric data of the user;
    using the sensors to measure one or more physical characteristics of the user; and
    transmitting the measured biometric data using the transmitter.

12. A method according to claim 11, wherein at least one of the sensors comprises a microphone, and the method further comprising the steps of measuring sound in the user's ear canal.

13. A method according to claim 12, wherein the microphone comprises a micro-actuator, the method further comprising measuring a back EMF signal.

14. A method according to claim 13, wherein the system includes a data processor, the method further including the step of converting the back EMF signal to an electrical signal and transmitting the electrical signal to the data signal processor.

15. A method according to claim 14, wherein the back EMF signal includes a first signal portion representative of the signal received from the system and a second signal representative of at least one physical characteristic of the user, the method further including the step of separating the first signal from the second signal.

16. A method according to claim 14, wherein the method further includes the step of transmitting the signal to a receiver external to the system.

17. A method according to claim 16, wherein the receiver comprises a smart phone.

18. A method according to claim 11, wherein at least one of the sensors comprises a skin contacting sensor or a non-skin contacting sensor.

19. A method according to claim 11, wherein at least one of the sensors comprises an umbo sensor, an eartip sensor, or a tethered sensor.

20. A method according to claim 11, wherein the output transducer is used as a sensor.

21. A method according to claim 20, wherein the sensor is used as a microphone to measure received sound at the tympanic membrane.

22. A method according to claim 21, wherein the signal from the microphone is coupled to the transmitter.

* * * * *